(12) United States Patent
Cary

(10) Patent No.: US 10,458,978 B2
(45) Date of Patent: Oct. 29, 2019

(54) MINIATURIZED LATERAL FLOW DEVICE FOR RAPID AND SENSITIVE DETECTION OF PROTEINS OR NUCLEIC ACIDS

(71) Applicant: Triad National Security, LLC, Los Alamos, NM (US)

(72) Inventor: Robert B. Cary, Santa Fe, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/431,705

(22) Filed: Feb. 13, 2017

(65) Prior Publication Data

US 2017/0160271 A1    Jun. 8, 2017

Related U.S. Application Data

(63) Continuation of application No. 15/012,804, filed on Feb. 1, 2016, now abandoned, which is a continuation
(Continued)

(51) Int. Cl.
*C12Q 1/68*     (2018.01)
*G01N 33/52*    (2006.01)
(Continued)

(52) U.S. Cl.
CPC ......... *G01N 33/523* (2013.01); *C12Q 1/6834* (2013.01); *C12Q 1/6837* (2013.01)

(58) Field of Classification Search
None
See application file for complete search history.

(56) References Cited

U.S. PATENT DOCUMENTS 3,667,607 A    6/1972  Brandt
4,235,601 A    11/1980 Deutsch et al.
(Continued)

FOREIGN PATENT DOCUMENTS

CN    1254844 A    5/2000
CN    1654214 A    8/2005
(Continued)

OTHER PUBLICATIONS

NanoComposix [retrieved on Jul. 27, 2017]: retrieved from the Internet: <URL: nanocomposix.com/pages/gold-colloid>.*
(Continued)

*Primary Examiner* — Robert T. Crow
(74) *Attorney, Agent, or Firm* — Cooley LLP

(57) ABSTRACT

The invention provides miniaturized lateral flow chromatographic and lateral flow chromatographic microarray devices (LFM). The miniaturization of lateral flow nucleic acid detection achieved by the present invention offers reduced reagent use, femtomole sensitivity, excellent linear dynamic range, and rapid detection. Moreover, the small feature sizes of capture oligonucleotides renders the potential information capacity of the platform comparable to more traditional spotted fluorescence microarrays as well as improving sensitivity. The LFM devices exemplified herein enable analytes to be detected within 10 seconds from the time of sample introduction to the LFM device. Sample volumes may be as low as about 10 microliters, significantly reducing assay costs and ameliorating reagent storage logistics. Additionally, the miniaturization of lateral flow opens the door to highly multiplexed assays, allowing many proteins or nucleic acids to be detected in a single assay.

18 Claims, 13 Drawing Sheets

Specification includes a Sequence Listing.

Related U.S. Application Data of application No. 11/894,910, filed on Aug. 22, 2007, now abandoned.

(60) Provisional application No. 60/925,210, filed on Apr. 18, 2007, provisional application No. 60/839,537, filed on Aug. 22, 2006.

(51) Int. Cl.
*C12Q 1/6834* (2018.01)
*C12Q 1/6837* (2018.01)

(56) References Cited

U.S. PATENT DOCUMENTS

| | | | |
|---|---|---|---|
| 4,663,277 A * | 5/1987 | Wang | G01N 33/54306 |
| | | | 435/5 |
| 4,683,195 A | 7/1987 | Mullis et al. | |
| 4,683,202 A | 7/1987 | Mullis | |
| 4,800,159 A | 1/1989 | Mullis et al. | |
| 4,960,691 A | 10/1990 | Gordon et al. | |
| 5,225,163 A | 7/1993 | Andrews | |
| 5,354,538 A | 10/1994 | Bunce et al. | |
| 5,514,785 A | 5/1996 | Van Ness et al. | |
| 5,516,664 A | 5/1996 | Hyman | |
| 5,578,467 A | 11/1996 | Schuster et al. | |
| 5,618,494 A | 4/1997 | Bunce et al. | |
| 5,716,819 A | 2/1998 | Chatterjee | |
| 5,736,188 A | 4/1998 | Alcock et al. | |
| 5,741,647 A | 4/1998 | Tam | |
| 5,922,617 A | 7/1999 | Wang et al. | |
| 6,007,999 A | 12/1999 | Clark | |
| 6,037,127 A | 3/2000 | Ebersole et al. | |
| 6,083,502 A * | 7/2000 | Pastan | A61K 49/0004 |
| | | | 424/133.1 |
| 6,146,589 A | 11/2000 | Chandler | |
| 6,190,612 B1 | 2/2001 | Berger et al. | |
| 6,214,587 B1 | 4/2001 | Dattagupta et al. | |
| 6,261,779 B1 | 7/2001 | Barbera-Guillem et al. | |
| 6,300,069 B1 | 10/2001 | Missel et al. | |
| 6,335,205 B1 * | 1/2002 | Bausback | G01N 33/558 |
| | | | 422/401 |
| 6,468,749 B1 | 10/2002 | Ulanovsky et al. | |
| 6,471,916 B1 | 10/2002 | Noblett | |
| 6,555,349 B1 | 4/2003 | O'Donnell | |
| 6,743,399 B1 | 6/2004 | Weigl et al. | |
| 7,094,536 B2 | 8/2006 | Kurn | |
| 7,159,618 B2 | 1/2007 | Broyer et al. | |
| 7,186,508 B2 | 3/2007 | Lee et al. | |
| 7,195,872 B2 | 3/2007 | Agrawal et al. | |
| 7,273,590 B2 | 9/2007 | Yao et al. | |
| 8,173,078 B2 | 5/2012 | Yao et al. | |
| 8,980,561 B1 | 3/2015 | Cai et al. | |
| 9,207,236 B2 | 12/2015 | Cary | |
| 9,354,199 B2 | 5/2016 | Selden et al. | |
| 9,428,781 B2 | 8/2016 | Cai et al. | |
| 9,944,922 B2 | 4/2018 | Cary | |
| 2001/0019825 A1 | 9/2001 | Lee et al. | |
| 2002/0028475 A1 | 3/2002 | Ligler et al. | |
| 2002/0058252 A1 * | 5/2002 | Ananiev | C12Q 1/6811 |
| | | | 435/6.11 |
| 2002/0076825 A1 | 6/2002 | Cheng et al. | |
| 2002/0127574 A1 * | 9/2002 | Mirkin | B82Y 15/00 |
| | | | 435/6.12 |
| 2002/0172969 A1 | 11/2002 | Burns et al. | |
| 2002/0177135 A1 * | 11/2002 | Doung | B01F 13/0059 |
| | | | 435/6.11 |
| 2002/0179445 A1 | 12/2002 | Alajoki et al. | |
| 2002/0192839 A1 | 12/2002 | Mink et al. | |
| 2003/0003514 A1 | 1/2003 | Kovalenko | |
| 2003/0008308 A1 | 1/2003 | Enzelberger et al. | |
| 2003/0044862 A1 | 3/2003 | Giaccia et al. | |
| 2003/0054176 A1 * | 3/2003 | Pantano | C03C 17/30 |
| | | | 428/429 |
| 2003/0064364 A1 | 4/2003 | Lockhart et al. | |
| 2003/0100128 A1 | 5/2003 | Kenjyou et al. | |
| 2003/0170686 A1 | 9/2003 | Hoet et al. | |
| 2003/0190608 A1 | 10/2003 | Blackburn | |
| 2004/0029177 A1 | 2/2004 | Nadaoka et al. | |
| 2004/0053256 A1 * | 3/2004 | Lee | C12Q 1/6816 |
| | | | 435/6.11 |
| 2004/0058378 A1 | 3/2004 | Kong et al. | |
| 2004/0086897 A1 * | 5/2004 | Mirkin | C12Q 1/6816 |
| | | | 435/6.12 |
| 2004/0110167 A1 | 6/2004 | Gerdes et al. | |
| 2004/0152122 A1 | 8/2004 | Hwang et al. | |
| 2004/0209309 A1 * | 10/2004 | Muldoon | C07K 16/18 |
| | | | 435/7.1 |
| 2005/0014192 A1 | 1/2005 | Kurn | |
| 2005/0032729 A1 | 2/2005 | Shyamala | |
| 2005/0032730 A1 | 2/2005 | Von Der Mulbe et al. | |
| 2005/0042627 A1 | 2/2005 | Chakrabarti et al. | |
| 2005/0047972 A1 * | 3/2005 | Lauks | B01L 3/50273 |
| | | | 422/501 |
| 2005/0079492 A1 | 4/2005 | Burgess, Jr. et al. | |
| 2005/0112780 A1 | 5/2005 | Song | |
| 2005/0136443 A1 | 6/2005 | Shigemori | |
| 2005/0221281 A1 | 10/2005 | Ho | |
| 2005/0227275 A1 | 10/2005 | Jung et al. | |
| 2005/0243321 A1 | 11/2005 | Cohen et al. | |
| 2005/0250141 A1 | 11/2005 | Lambert et al. | |
| 2006/0024813 A1 | 2/2006 | Warthoe | |
| 2006/0041058 A1 | 2/2006 | Yin et al. | |
| 2006/0127886 A1 | 6/2006 | Kaylor et al. | |
| 2006/0154286 A1 | 7/2006 | Kong et al. | |
| 2006/0160078 A1 | 7/2006 | Cardy et al. | |
| 2006/0177873 A1 | 8/2006 | Dowd | |
| 2006/0239859 A1 | 10/2006 | Ohman et al. | |
| 2006/0246601 A1 | 11/2006 | Song et al. | |
| 2006/0286570 A1 | 12/2006 | Rowlen et al. | |
| 2007/0015166 A1 | 1/2007 | Nilsen | |
| 2007/0020768 A1 | 1/2007 | Rundstrom et al. | |
| 2007/0039835 A1 | 2/2007 | Rossier et al. | |
| 2007/0231798 A1 | 10/2007 | Collins | |
| 2008/0124720 A1 | 5/2008 | Sowerby et al. | |
| 2008/0145835 A1 | 6/2008 | Alajem et al. | |
| 2008/0207892 A1 | 8/2008 | Iwaki | |
| 2008/0280285 A1 | 11/2008 | Chen et al. | |
| 2009/0047673 A1 | 2/2009 | Cary | |
| 2009/0053106 A1 | 2/2009 | Wu et al. | |
| 2009/0130719 A1 | 5/2009 | Handique | |
| 2009/0181411 A1 | 7/2009 | Battrell et al. | |
| 2009/0186357 A1 | 7/2009 | Mauk et al. | |
| 2009/0246782 A1 | 10/2009 | Kelso et al. | |
| 2010/0203532 A1 | 8/2010 | Makrigiorgos | |
| 2010/0248273 A1 | 9/2010 | Campbell et al. | |
| 2010/0276005 A1 | 11/2010 | Allain et al. | |
| 2011/0039261 A1 | 2/2011 | Hillebrand et al. | |
| 2011/0117540 A1 | 5/2011 | Cary | |
| 2011/0160090 A1 | 6/2011 | Cary | |
| 2014/0045191 A1 | 2/2014 | DeJohn et al. | |
| 2014/0141484 A1 | 5/2014 | Campbell et al. | |
| 2015/0184255 A1 | 7/2015 | Cai et al. | |
| 2016/0083716 A1 | 3/2016 | Cary | |
| 2016/0222442 A1 | 8/2016 | Cary | |
| 2016/0310948 A1 | 10/2016 | Nowakowski et al. | |
| 2016/0362725 A1 | 12/2016 | Cai et al. | |
| 2017/0233794 A1 | 8/2017 | Cai et al. | |
| 2018/0304260 A1 | 10/2018 | Thomas et al. | |

FOREIGN PATENT DOCUMENTS

| | | |
|---|---|---|
| CN | 1954214 A | 4/2007 |
| CN | 10140993 | 4/2009 |
| EP | 0805215 A2 | 5/1997 |
| EP | 1972938 A1 | 9/2008 |
| GB | 2261284 A | 5/1993 |
| JP | 05240872 | 9/1993 |
| JP | 2001518614 | 10/2001 |
| JP | 2005185972 | 7/2005 |
| JP | 2005532827 | 11/2005 |
| JP | 2006520190 | 9/2006 |
| JP | 2007503958 | 3/2007 |

(56) References Cited

FOREIGN PATENT DOCUMENTS

| JP | 2008521432 | | 6/2008 |
|---|---|---|---|
| JP | 2009100761 | | 5/2009 |
| NO | WO2007030505 | | 3/2007 |
| WO | 9423055 | | 10/1994 |
| WO | 9703207 | | 1/1997 |
| WO | 0029112 | | 5/2000 |
| WO | WO2004007078 | A1 | 1/2004 |
| WO | 2004090555 | A1 | 10/2004 |
| WO | 2004092342 | A2 | 10/2004 |
| WO | WO2005098439 | A2 | 10/2005 |
| WO | WO2006059911 | A1 | 6/2006 |
| WO | 2006098804 | | 9/2006 |
| WO | 2006122311 | A2 | 11/2006 |
| WO | 2007083388 | | 7/2007 |
| WO | WO2008105814 | A2 | 9/2008 |
| WO | 2009103843 | A2 | 8/2009 |
| WO | WO2009137059 | A2 | 11/2009 |
| WO | WO2010037012 | A2 | 4/2010 |
| WO | 2010105074 | A1 | 9/2010 |
| WO | 2011087813 | A2 | 7/2011 |
| WO | 2012083189 | A2 | 6/2012 |
| WO | WO 2012/145725 | A2 | 10/2012 |
| WO | WO2012145730 | A2 | 10/2012 |

OTHER PUBLICATIONS

Goda et al, Sensors, vol. 13, pp. 2267-2278. (Year: 2013).*
Kane et al, Nuclec Acids Res., vol. 28, pp. 4552-4557. (Year: 2000).*
"Jikken Igaku Bessatsu Mokuteki De Eraberu PCR Jikken Protocol", Jan. 1, 2011, 50-53.
"Kodak DCS Quick Start Guide", 2005.
"Microarray technology: An array of opportunities", Nature, Apr. 25, 2002, 885-891.
"PCR Amplification", Protocols and Applications Guide, https://www.promega.ca/resources/product-guides-and-selectors/protocols-and-applications-guide/pcr-amplification/, 2016.
Akane, et al., "Identification of the Heme Compound Copurified with Deoxyribonucleic Acid (DNA) from Bloodstains, a Major Inhibitor of Polymerase Chain Reaction (PCR) Amplification1'", Journal of Forensic Sciences, Mar. 1994, 362-372.
Albretsen, et al., "Optimal Conditions for Hybridization with Oligonucleotides: A Study with myc-Oncogene DNA Probes", Analytical Biochemistry, 1988, 193-202.
Al-Soud, et al., "Effects of Amplification Facilitators on Diagnostic PCR in the Presence of Blood, Feces, and Meat", Dec. 2000, 4463-4470.
An, et al., "Characterization of a Thermostable UvrD Helicase and Its Participation in Helicase-dependent Amplification", The Journal of Biological Chemistry, Aug. 12, 2005, 28952-28958.
Andreotti, et al., "Immunoassay of infectious agents", BioTechniques Euro Edition, Oct. 2003, 850-859.
Ausbel, et al., "Current Protocols in Molecular Biology", John Wiley & Sons, Inc., 1992, 15.6.1-15.6.4.
Aveyard, et al., "One step visual detection of PCR products with gold nanoparticles and a nucleic acid lateral flow (NALF) device", Chem. Commun., 2007, 4251-4253.
Baeumner, et al., "A rapid biosensor for viable B. anthracis spores", Anal. Bioanal. Chem., 2004, 15-23.
Baeumner, et al., "A Universal Nucleic Acid Sequence Biosensor with Nanomolar Detection Limits", Analytical Chemistry, Feb. 15, 2004, 888-894.
Baeumner, et al., "Biosensor for Dengue Virus Detection: Sensitive, Rapid, and Serotype Specific", Analytical Chemistry, Mar. 15, 2002, 1442-1448.
Baeumner, "Biosensors for environmental pollutants and food contaminants", Anal Bioanal Chem, 2003, 434-445.
Barany, "The Ligase Chain Reaction in a PCR World", Genome Research, Aug. 1991, 5-16.

Baskaran, et al., "Uniform Amplification of a Mixture of Deoxyribonucleic Acids with Varying GC Content", Genome Research, Jul. 1996, 633-638.
Berthelet, et al., "Rapid, direct extraction of DNA from soild for PCR analysis using polyvinylpyrrolidone spin columns", FEMS Microbiology Letter, 1996, 17-22.
Biagini, et al., "Rapid, Sensitive, and Specific Lateral-Flow Immunochromatographic Device to Measure Anti-Anthrax Protective Antigen Immunoglobulin G in Serum and Whole Blood", Clinical and Vaccine Immunology, May 2006, 541-546.
Blake, et al., "Thermodynamic effects of formamide on DNa stability", Nucleic Acids Research, 1996, 2095-2103.
Boom, et al., "Rapid and Simple Method for Purification of Nucleic Acids", Journal of Clinical Microbiology, Mar. 1990, 495-503.
Boom, et al., "Rapid Purification of Hepatitis B Virus DNA from Serum", Journal of Clinical Microbiology, Sep. 1991, 1804-1811.
Braasch, et al., "Locked nucleic acid (LNA): fine-tuning the recognition of DNa and RNA", Chemistry & Biology, 2001, 731-735.
Braun, et al., "Exponential DNA Replication by Laminar Convection", Physical Review Letters, Oct. 10, 2003, 158103-1-158103-4.
Bright, et al., "Incidence of adamantane resistance among influenza A (H3N2) viruses isolated worldwide from 1994 to 2005: a cause for concern", Lancet, Sep. 22, 2005, 1175-1181.
Brlansky, et al., "Colonization of the Sharpshooter Vectors, Oncometopia nigricans and Homalodisca coagulata, by Xylem-LOimited Bacteria", Phytopathology, 1983, 530.535.
Brlansky, et al., "Transmission of the Citrus Variegated Chlorosis Bacterium Xylella fastidiosa with the Sharpshooter Oncometopia nigricans", Plant Disease, Nov. 2002, 1237-1239.
Buck, et al., "Design Strategies and Performance of Custom DNA Sequencing Primers", BioTechniques, 1999, 528-536.
Buhro, et al., "Semiconductor nanocrystals: Shapematters", Nature Materials, Mar. 2003, 138-139.
Burns, et al., "An Integrated Nanoliter DNA Analysis Device", Science, Oct. 16, 1998, 484-487.
Capaldi, et al., "Signal amplification through nucleotide extension and excision on a dendritic DNA platform", Nucleic Acids Research, 2000, i-vii.
Carney, et al., "Present and future applications of gold in rapid assays", IVD Technology, Mar. 1, 2006, 1-8.
Carter, et al., "Lateral flow microarrays: a novel platform for rapid nucleic acid detection based on miniaturized lateral flow chromatography", Nucleic Acids Research, 2007, 1-11.
Caruthers, et al., "Helicase structure and mechanism", Curr Opin Struc Biol, 2002, 123-133.
Cary, "An Integrated Low Cost Nucleic Acid Analysis Platform for the Rapid Detection of Plan Pathogens", Jan. 6, 2011.
Chang, et al., "Culture and Serological Detection of the Xylem-Limited Bacterium Causing Citrus Variegated Chlorosis and Its Identification as a Strain of Xylella fastidiosa", Current Microbiology, 1993, 137-142.
Chanteau, et al., "Early diagnosis of bubonic plague using F1 antigen capture ELISA assay and rapid immunogold dipstick", Int. J. Med. Microbiol., 2000, 279-283.
Cheek, et al., "Chemiluminescence Detection for Hybridization Assays on the Flow-Thru Chip, a Three-Dimensional Microchannel Biochip[", Analytical Chemistry, Dec. 15, 2001, 5777-5783.
Cheng, et al., "Chip PCR. II. Investigation of different PCR amplification systems in Microfabricated silicon-glass chips", Nucleic Acids Research, 1996, 380-385.
Chin, et al., "Lab-on-a-chip devices for global health: Past Studies and future opportunities", Lab Chip, 2007, 41-57.
Ciapina, et al., "A nested-PCR assay for detection of Xylella fastidiosa in citrus plants and sharpshooter leafhoppers", Journal of Applied Microbiology, 2004, 546-551.
Cirino, et al., "Multiplex diagnostic platforms for detection of biothreat agents", Expert Rev. Mol. Diagn., 2004, 841-857.
Collins, "Purification and characterization of Thermus thermophilus UvrD", Extremophiles, 2003, 35-41.
Compton, "Nucleic acid sequence-based amplification", Nature, Mar. 7, 1991, 91-92.
Cook, et al., "Synthesis and hybridization of a series of biotinylated oligonucleotides", Nucleic Acids Research, 1988, 4077-4095.

(56) References Cited

OTHER PUBLICATIONS

Corstjens, et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, 2001, 1885-1893.
Cubero, et al., "Genetic Relationship among Worldwide Strains of Xanthomonas Causing Canker in Citrus Species and Design of New Primers for Their Identification by PCR", Applied and Environmental Microbiology, Mar. 2002, 1257-1264.
Cubero, et al., "Quantitative PCR Method for Diagnosis of Citrus Bacterial Canker", Applied and Environmental Microbiology, Jun. 2001, 2849-2852.
Davis, et al., "Pierce's Disease of Grapevines: Isolation of the Causal Bacterium", Science, Jan. 6, 1978, 775-778.
Dawson, et al., "Identification of A/H5N1 Influenza Viruses Using a Single Gene Diagnostic Microarray", Anal. Chem., 2007, 378-384.
Kieleczawa, et al., "DNA Sequencing by Primer Walking with Strings of Continguous Hexamers", Science, Dec. 11, 1992, 1787-1791.
Kievits, et al., "NASBA (TM) isothermal enzymatic in vitro nucleic acid amplification optimzed for the diagnosis of HIV-1 infection", Journal of Virological Methods, 1991, 273-286.
Kilbourne, et al., "The total influenza vaccine failure of 1947 revisited: Major intrasubtypic antigenic change can explain failure of vaccine in a post-World War II epidemic", PNAS, Aug. 6, 2002, 10748-10752.
Kimura, et al., "One-step immobilization ofr poly(dT)-modified DNA onto non-modified plastic substrates by UV irradiation for microarrays", Biochemical and Biophysical Research Communications, 2006, 477-484.
Koch, "Technology Platforms for Pahrmacogenomic Diagnostic Assays", Nature Reviews Drug Discovery, Sep. 2004, 749-761.
Kohn, "An Immunochromatographic Technique", Immunology, 1968, 863-865.
Koonjul, "Inclusion of polyvinylpyrrolidone in the polymerase chain reaction reverses the inhibitory effects of polyphenolic contamination of RHNA", Nucleic Acids Research, 1999, 915-916.
Kornberg, et al., DNA Replication, 1992, 298-299; 356-365.
Kozwich, et al., "Development of a Novel, Rapid Integrated Cryptosporidium Parvum Detection Assay", Applied and Environmental Microbiology, Jul. 2000, 2711-2717.
Kwoh, et al., "Transcription-based amplification system and detection of amplified human immunodeficiency virus type 1 with a bead-based sandwich hybridization format", Proc. Natl. Acad. Sci. USA, Feb. 1989, 117301177.
Landegren, et al., "A Ligase-Mediated Gene Detection Technique", Science, Aug. 26, 1988, 1077-1080.
Lane, et al., "The thermodynamic advantage of DNA oligonucleotide 'stacking hybridization' reactions: energetics of a DNA nick", Nucleic Acids Research, 1997, 611-616.
Leone, et al., "Direct detection of potato leafroll virus in potato tubers by immunocapture and the isothermal nuclic acid amplification method NASBA", Journal of Virological Methods, 1997, 19-27.
Liao, et al., "Miniature RT-PCT system for diagnosis of RNA-based viruses", Nucleic Acids Research, Oct. 12, 2005, 1-7.
Lim, et al., "Current and Developing Technologies for Monitoring Agents of Bioterrorism and Biowarfare", Clinical Microbiology Reviews, Oct. 2005, 583-607.
Liu, et al., "Self-Contained, Fully Integrated Biochip for Sample Preparation, Polymerase Chain Reaction Amplification and DNA Microarray Detection", Anal. Chem., vol. 76, 2004, 1824-1831.
Lockley, et al., "Calorimetric detection of immobilised PCR products generated on a solid support", Nucleic Acids Research, 1997, 1313-1314.
Loens et al., "Evaluation of NucliSens easyMAG for Automated Nucleic Acid Extraction from Various Clinical Specimens", Journal of Clinical Microbiology, Feb. 2007, 421-425.
Lonnberg, et al., "Chromatographic performance of a thin microporous bed of nitrocellulose", Journal of Chromatography B, 2001, 107-120.
Lowe, et al., "Multiplexed, Particle-Based Detection of DNa Using Flow Cytometry with 3DNA Dendrimers for Signal Amplification", Cytometry Part A, 2004, 135-144.
Mackay, "Real-time PCR in the microbiology laboratory", Clin Microbial Infect., 2004, 190-212.
Malek, et al., "Nucleic acid sequence-based amplification (NASBA)", Protocols for Nucleic Acid Analysis by Nonradioactive Probes, ed. Peter G. Isaac, 1994, 253-260.
Masny, et al., "Ligation mediated PCR performed at low denaturation temperatures—PCT melting profiles", Nucleic Acids Research, 2003, 1-6.
Michalet, et al., "Properties of Fluorescent Semiconductor Nanocrystals and their Application to Biological Labeling", Single Mol., 2001, 261-276.
Miyoshi, et al., "Molecular Crowding Regulates the Structural Switch of the DNA G-Quadruplex", Biochemistry, Nov. 20, 2002, 15017-15024.
Monteiro, et al., "Complex Polysaccharides as PCR Inhibitors in Feces: Helicdobacter pylori Model", Journal of Clinical Microbiology, Apr. 1997, 995-998.
Mumford, et al., "Rapid single-tube immunocapture RT-PCT for the detection of two yam potyviruses", Journal of Virological Methods, 1997, 73-79.
Musso, et al., "Betaine, Dimethyl Sulfoxide, and 7-Deaza-dGTP, a Powerful Mixture for Amplification of GC-Rich DNA Sequences", Journal of Molecular Diagnostics, Nov. 2006, 544-550.
Nicholson, et al., "Influenza", The Lancet, Nov. 22, 2003, 1733-1745.
O'Meara, et al., "Capture of Single-Stranded DNa Assisted by Oligonucleotide Modules", Analytical Biochemistry, 1998, 195-203.
O'Meara, et al., "Cooperative Oligonucleotides Mediating Direct Capture of Hepatitis C Virus RNa from Serum", Journal of Clinical Microbiology, Sep. 1998, 2454-2459.
Palese, et al., "Influenza vaccines: present and future", The Journal of Clinical Investigation, Jul. 2002, 9-13.
Pannucci, et al., "Virulence signatures: microarray-based approaches to discovery and analysis", Biosensors and Biolelectronics, 2004, 706-718.
Pastinen, et al., "A System for Specific, High-throughput Genotyping by Allele-specific Primer Extension on Microarrays", Genome Research, 2000, 1031-1042.
Pemov, et al., "DNA analysis with multiplex microarray-enhanced PCR", Nucleic Acid Research, 2005, 1-9.
Petrik, "Diagnostic applications of microarrays", Transfusion Medicine, 2006, 233-247.
Peytavi, et al., "Microfluidic Device for Rapid (<15 min) Automated Microarray Hybridization", Clinical Chemistry, 2005, 1836-1844.
Piepenburg, et al., "DNA Detection Using Recombination Proteins", PLoS Biology, Jul. 2006, 1115-1121.
Pooler, et al., "Detection of Xylella fastidiosa in potential insect vectors by immunomagnetic separation and nested polymerase chain reaction", Letters in Applied Microbiology, 1997, 1230126.
Pooler, et al., "Specifric PCR Detection and Identification of Xylella fastidiosa Strains Causing Citrus Variegated Chlorosis", Current Microbiology, 1995, 377-381.
Pristoupil, "Microchromatography and Microelectrophoresis on Nitrocellulose Membranes", Chromatographic Reviews, 1970, 109-125.
Purcell, et al., "Fate of Pierce's Disease Strains of Xylella fastidiosa in Common Riparian Plants in Califomiat", Plant Disease, 1999, 825-830.
Purcell, et al., "Pierce's Disease Bacterium: Mechanism of Transmission by Leafhopper Vectors", Science, Nov. 16, 1979, 839-841.
Ralser, et al., "An efficient and economic enhancer mix for PCR", Biochemical and Biophysical Research Communications, 2006, 747-751.
Rao, et al., "Developing rapid, point-of-care, multiplex detection for use in lateral flow devices", Smart Medical and Biomedical Sensor Technology III, Proc. of SPIE, 2005.

(56) References Cited

OTHER PUBLICATIONS

Rapley, "Enhancing PCR Amplification and Sequencing Using DNA-Binding Proteins", Molecular Biotechnology, Dec. 1994, 295-298.

Reinhartz, et al., "A novel rapid hybridization technique: paper chromatography hybridization assay (PACHA)", Gene, 1993, 221-226.

Rodriguez, et al., "Detection and Diversity Assessment of Xylella fastidiosa in Field-Collected Plant and Insect Samples by Using 16S rRNA and gyrB Sequences", Applied and Environmental Microbiology, Jul. 2003, 4249-4255.

Romero, et al., "Amplification and cloning of a long RNA virus genome using immunocapture-long RT-PCR", Journal of Virological Methods, 1997, 159-163.

Roper, et al., "Advances in Polymerase Chain Reaction on Microfluidic Chips", Analytical Chemistry, 2005, 3887-3894.

Day, et al., "Immobilization of polynucleotides on magnetic particles", Biochem. J., 1991, 735-740.

De Jong, et al., "Oseltamivir Resistance during Treatment of Influenza A (H5N1) Infection", New England Journal of Medicine, Dec. 22, 2005, 2667-2672.

Deiman, et al., "Characteristics and Applications of Nucleic Acid Sequence-Based Amplification (NASBA)", Molecular Biotechnology, 2002, 163-179.

Dineva, et al., "Simultaneous Visual Detection of Multiple Viral Amplicons by Dipstick Assay", Journal of Clinical Microbiology, Aug. 2005, 4015-4021.

Dobkin, et al., "RNA Replication: Required Itermediates and the Dissociation of Template, Product, and QB Replicase", Biochemistry, 1979, 2038-2044.

Dong, et al., "A coupled complex of T4 DNA replication helicase (gp41) and polymerase (gp43) can perform rapid and processive DNA strand-displacement synthesis", Proc. Natl. Acad. Sci. USA, Dec. 1996, 14456-14461.

Duck, et al., "Probe Amplifier System Based on Chimeric Cycling Oligonucleotides", Biotechniques, 1990, 142-148.

Easterday, et al., "Specific detection of Bacillus Anthracis using a TaqMan mismatch amplification mutation assay", BioTechniques, 2005, 731-735.

Easterday, et al., "Use of Single Nucleotide Polymorphisms in the plxR Gene for Specific Identification of Bacillus Anthracis", Journal of Clinical Microbiology, Apr. 2005, 1995-1997.

Edwards, et al., "Optimization of DNA-tagged dye-encapsulating liposomes for lateral-flow assays based on sandwich hybridization", Anal. Bioanal. Chem., 2006, 1335-1343.

Elliott, et al., "Use of laser microdissection greatly improves the recovery of DNA from sperm on microscope slides", Forensic Science International, 2003, 28-36.

Findlay et al., "Automated Closed-Vessel System for inVitro Diagnostics Based on Polymerase Chain Reaction", Clinical Chemistry, 1993, 1927-1933.

Fisher, et al., "Development of a Quantum Dot-Lateral Flow Assay", BEACON e-news at Jet Propulsion Laboratory, 2003.

Fong, et al., "Rapid Solid-Phase Immunoassay for Detection of Methicillin-Resistant *Staphylococcus aureus* Using Cycling Probe Technology", Journal of Clinical Microbiology, Jul. 2000, 2525-2529.

Frackman, et al., "Betaine and DMSO: Enhancing Agents for PCR", Promega Notes, 1998, 27.

Fu, et al., "Controlled reagent transport in disposable 2D paper networks", Lab Chip, 2010, 918-920.

Fukuta, et al., "Development of immunocapture reverse transcription loop-mediated isothermal amplification for the detection of tomato spotted wilt virus from chrysanthemum", Journal of Virological Methods, 2004, 49-55.

Gani, et al., "Potential Impact of Antiviral Drug Use during Influenza Pandemic", Emerging Infectious Diseases, Sep. 2005, 1355-1362.

Gill, et al., "An investigation of the rigor of interpretation rules for STRs derived from less than 100 pg of DNA", Forensic Science International, 2000, 17-40.

Gill, "Application of Low Copy Number DNA Profiling", Croatian Medical Journal, 2001, 228-232.

Glynou, et al., "Oligonucleotide-Functionalized Gold Nanoparticles as Probes in a Dry-Reagent Strip Biosensor for DNA Analysis by Hybridization", Analytical Chemistry, Aug. 15, 2003, 4155-4160.

Goheen, et al., "Association of a Rickettsialike Organism with Pierce's Disease of Grapevines and Alfalfal Swarf and Heat Therapy of the Disease in Grapevines", Phytopathology, Mar. 1973, 341-345.

Goldmeyer, et al., "Development of a Novel One-Tube Isothermal Reverse Transcription Thermophilic Helicase-Dependent Amplification Platform for Rapid RNA Detection", Journal of Molecular Diagnostics, Nov. 2007, 639-644.

Grainge, et al., "Biochemical analysis of components of the pre-replication complex of Archaeoglobus fulgidus", Nucleic Acids Research, 2003, 4888-4898.

Groody, "Detection of Foodborne Pathogens Using DNA Probes and a Dipstick Format", Molecular Biotechnology, 1996, 323-327.

Guatelli, et al., "Isothermal, in vitro amplification of nucleic acids by a multienzyme reaction modeled after retroviral replication", Proc. Natl. Acad. Sci. USA, Mar. 1990, 1874-1878.

Guo, et al., "Direct fluorescence analysis of genetic polymorphisms by hybridization with oligonucleotide arrays on glass supports", Nucleic Acids Research, 1994, 5456-5465.

Harmon, et al., "Biochemical Characterization of the DNA Helicase Activity of the *Escherichia coil* RecQ Helicase", The Journal of Biological Chemistry, 2001, 232-243.

Hartley, et al., "Biosensor for the specific detection of a single viable B. Anthracis spore", Anal. Bioanal. Chem., 2003, 319-327.

Hartung, et al., "Detection of *Xanthomonas campestris* pv. Citri by the Polymerase Chain Reaction Method", Applied and Environmental Microbiology, Apr. 1993, 1143-1148.

Hartung, et al., "Rapid and Sensitive Colorimetric Detection of *Xanthomonas axonopodis* pv. citri by Immunocapture and a Nested-Polymerase Chain Reaction Assay", Phytopathology, 1996, 95-101.

Heller, "DNA microarray technology: devices, systems, and applications", Annu. Rev. Biomed. Eng., 2002, 129-153.

Hendson, et al., "Genetic Diversity of Pierce's Disease Strains and Other Pathotypes of Xylella Fastidiosa", Applied and Environmental Microbiology, Feb. 2001, 895-903.

Henegariu, et al., "Multiplex PCR: Critical Parameters and Step-by-Step Protocol", BioTechniques, 1997, 504-511.

Hill, et al., "Acquisition and Retention of Xylella Fastidiosa by an Efficient Vector, Graphocephala atropunctata", Phytopathology, 1997, 209-212.

Hill, et al., "Fluorescent Amplified Fragment Length Polymorphism Analysis of Bacillus anthracis, Bacillus cereus, and Bacillus thuringiensis Isolates", Applied and Environmental Microbiology, Feb. 2004, 1068-1080.

Hill, et al., "Populations of Xylella fastidiosa in Plants Required for Transmission by an Efficient Vector", Phytopathology, 1997, 1197-1201.

Hopkins, "Xylella Fastidiosa: Xylem-Limited Bacterial Pathogen of Plants", Ann. Rev. Phytopathol., 1989, 271-290.

Huber, et al., "Accessing Single Nucleotide Polymorphisms in Genomic DNA by Direct Multiplex Polymerase Chain Reaction Amplification on Oligonucleotide Microarrays", Analytical Biochemistry, 2002, 25-33.

Huckle, "Point-of-care diagnostices: will the hurdles be overcome this time?", Expert Review of Medical Devices, 2006, 421-426.

Jakobashvili, et al., "Low temperature cycled PCR protocol for Klenow fragment of DNA polymerase I in the presence of proline", Nucleic Acids Research, 1999, 1566-1568.

Ilyushina, et al., "Detection of amantadine-resistant variants among avian influenza viruses isolated in North America and Asia", Virology, 2005, 102-106.

Jacobi, et al., "Development of a multiplex immunocapture RT-PCR assay for detection and differentiation of tomato and tobacco mosaic tobamoviruses", Journal of Virological Methods, 1998, 167-178.

(56) References Cited

OTHER PUBLICATIONS

Jacobsen, et al., "Direct isolation of poly(A)+ RNA from 4 M guanidine thiocyanate-lysed cell extracts using locked nucleic acid-oligo(T) capture", Nucleic Acid Research, 2004, 1031-1042.

Jensen, et al., "DMSO and Betaine Greatly Improve Amplification of GC-Rich Constructs in De Novo Synthesis", PLoS One, Jun. 11, 2010, e11024.

Jobling, et al., "Encoded Evidence: DNA in Forensic Analysis", Nature Reviews: Genetics, Oct. 2004, 739-751.

Kandimalla, et al., "Design, biochemical, biophysical and biological properties of cooperative antisense oligonucleotides", Nucleic Acids Research, 1995, 3578-3584.

Kaplan, et al., "DnaB from Thermus aquaticus Unwinds Forked Duplex DNA with an Asymmetric Tail Length Dependence", The Journal of Biological Chemistry, Mar. 12, 1999, 6889-6897.

Kempitiya, et al., "Localized microwave heating in microwells for parallel DNA amplification applications", Applied Physics Letters, 2009, 064106-1-064106-3.

Keohavong, et al., "Fidelity of DNa polymerases in DNA amplification", Proc. Natl. Acad. Sci. USA, Dec. 1989, 9253-9257.

Rouse, et al., "Microarray technology—an intellectual property retrospective", Pharmacogenomics, 2003, 1462-2416.

Rule, et al., "Rapid method for visual identification of specific DNA sequences based on DNA-tagged liposomes", Clinical Chemistry, 1996, 1206-1209.

Saki, et al., "Primer-Directed Enzymatic Amplification of DNA with a Thermostable DNA Poymerase", Science, Jan. 29, 1988, 487-491.

Sambrook, et al., Molecular Cloning: A Laboratory Manual, 2001, 9.47-9.55.

Sarkar, et al., "Formamide can dramatically improve the specificity of PCR", Nucleic Acids Research, Dec. 25, 1990, 7465.

Schildkraut, et al., "Dependence of the Melting Temperature of DNA on Salt Concentration", Biopolymers, 1965, 195-208.

Schwab, et al., "Immunoaffinity concentration and purification of waterborne enteric viruses for detection by reverse transcriptase PCR", 1996, 2086-2094.

Shoffner, et al., "Chip PCR. I. Surface passivation of microfabricated silicon-glass chips for PCR", Nucleic Acids Research, 1996, 375-379.

Singh, et al., "LNA (locked nucleic acids): synthesis and high-affinity nucleic acid recognition", Chem. Commun., 1998, 455-456.

Spiess, "Trehalose Is a Potent PCR Enhancer Lowering of DNA Melting Temperature and Thermal Stabilization of Taq Polymerase by the Disaccharide Trehalose", Clinical Chemistry, Jul. 2004, 1256-1259.

Spiro, et al., "A Bead-Based Method for Multiplexed Identification and Quantitation of DNA Squences Using Flow Cytometry", Applied and Environmental Microbiology, Oct. 2000, 4258-4265.

Stears, et al., "A novel, sensitive detection system for high-density microarrays using dendrimer technology", Physiol. Genomics, 2000, 93-99.

Sterne, "The use of Anthrax Vaccines Prepared from Avirulent (Uncapsulated) Variants of Bacillus anthracis", Onderstepoort Journal of Veterinary Science and Animal Industry, Oct. 1939, 307-312.

Stiver, "The treatment of influenza with antiviral drugs", CMAJ, Jan. 7, 2003, 49-57.

Sunen, et al., "Recovery and detection of enterovirus, hepatits A virus and Norwalk virus in hardshell clams (*Mercenaria mercenaria*) by RT-PCT methods", Journal of Virological Methods, 1999, 179-187.

Tennikova, et al., "An Introduction to Monolithic Disks as Stationary Phases for High Performance Biochromatography", J. High Resol. Chromatogr., 2000, 27-38.

Tennikova, et al., "High-performance membrane chromatography: highly efficient separation method for proteins in ion-exchange, hydrophobic interaction and reversed-phase models", Journal of Chromatography, 1993, 279-288.

Thommes, et al., "Membrane Chromatography—An Integrative Concept in the Downstream Processing of Proteins", Biotechnol. Prog., 1995, 357-367.

Tsai, et al., "Rapid Method for Separation of Bacterial DNA from Humic Substances in Sediments for Polymerase Chain Reaction", Applied and Environmental Microbiology, Jul. 1992, 2292-2295.

Van Ness, et al., "Isothermal reactions for the amplification of oligonucleotides", PNAS, Apr. 15, 2003, 4504-4509.

Vincent, et al., "Helicase-dependent isothermal DNa amplification", EMBO Reports, 2004, 795-800.

Wahlestedt, et al., "Potent and nontoxic antisense oligonucleotides containing locked nucleic acids", PNAS, May 9, 2000, 5633-5638.

Walker, et al., "Isothermal in vitro amplification of DNA by a restriction enzyme/DNA apolymerase system", Proc. Natl. Acad. Sci. USA, Jan. 1992, 392-396.

Walker, et al., "Strand displacement amplification—an isothermal, in vitro DNA amplification technique", Nucleic Acid Research, 1992, 1691-1696.

Wang, et al., "Droplet-based micro oscillating-flow PCR chip", Journal of Micromechanics and Microengineering, 2005, 1369-1377.

Webby, et al., "Are we ready for pandemic influenza?", Science, Nov. 28, 2003, 1519-1522.

Webster, et al., "Potential Impact of Antiviral Drug Use during Influenza Pandemic", American Scientist, 2003, 122-129.

Wei, et al., "Using a microfluidic device for 1 ul DNA micrarray hybridization in 500 s", Nucleic Acids Research, 2005, 1-11.

Weighardt, et al., "A Simple Procedure for Enhancing PCR Specificity", PCR Methods and Applications, Aug. 1, 1993, 77-81.

Wells, et al., "Isolation, Culture, and Pathogenicity of the Bacterium Causing Phony Disease of Peach", Phytopathology, 1983, 859-862.

Wetzel, et al., "A highly sensitive immunocapture polymerase chain reaction method for plum pox potyvirus detection", Journal of Virological Methods, Jul. 1992, 27-37.

Wickenheiser, "Trace DNA: A Review, Discussion of Theory, and Application of the Transfer of Trace Quantities of DNA Through Skin Contact", J Forensic Sci, 2002, 442-450.

Wilding, et al., "PCR in a Silicon Microstructure", Clinical Chemistry, 1994, 1815-1818.

Wilson, "Inhibition and Facilitation of Nucleic Acid Amplification", Applied and Environmental Microbiology, 1997, 3741-3751.

Yang, et al., "PCR-based diagnositcs for infectious diseases: uses, limitations, and future applications in acute-care settings", The Lancet Infectious Diseases, Jun. 2004, 337-348.

Young, et al., "Polyvinylpyrrolidone-Agarose Gel Electrophoresis Purification of Polymerase Chain Reaction-Amplifiable DNA from Soils", Applied and Environmental Microbiology, Jun. 1993, 1972-1974.

Zaytseva, et al., "Multi-analyte single-membrane biosensor for the serotype-specific detection of Dengue virus", Anal. Bioanal. Chem., 2004, 46-53.

Zeng, et al., "High GC Amplification: A Comparative Study of Betaine, DMSO, Formamide and Glycerol as Additives", Life Science Journal, 2006, 67-71.

Zhang, et al., "PCR microfluidic devices for DNA amplification", Biotechnology Advances, 2006, 243-284.

Zijlmans, et al., "Detection of Cell and Tissue Surface Antigens Using Up-Converting Phosphors: A New Reporter Technology", Analytical Biochemistry, 1999, 30-36.

Zuiderwijk, et al., "An amplication-free hybridization-based DNA assay to detect *Streptococcus pneumoniae* utilizing the up-convewrting phosphor technology", Clinical Biochemistry, 2003, 401-403.

Huang, et al., "A Capillary-Driven Microfluidic Device for Rapid DNA Detection with Extremely Low Sample Consumption", 17th International Conference on Miniaturized Systems for Chemistry and Life Science, Freiburg, Germany, Oct. 27-31, 2013, 191-193.

Barnes, "PCR amplification of up to 35-kb DNA with high fidelity and high yield from a bacteriophage templates", Proc. Natl. Acad. Sci., vol. 91, Mar. 1994, 2216-2220.

Eggerding, "A One-step Coupled Amplification and Oligonucleolide Ligation Procedure for Multiplex Genetic Typing", PCR Methods and Applications, Cold Spring Harbor Laboratory Press, 1995, 337-345.

(56) References Cited

OTHER PUBLICATIONS

Henke et al., "Betaine improves the PCR amplification of GC-rich DNA sequences", Nucleic Acids Research, vol. 25, No. 19, Oxford University Press, 1997, 3957-3958.

Hutton, et al., "Activity of Endonuclease S1 in Denaturing Solvents: Dimethylsulfoxide, Dimethylformamide, Formamide and Formaldehyde", Biochemical and Biophysical Research Communications, vol. 66, No. 3, Academic Press, Inc., 1975, 942-948.

Kim et al., "Recombinant fragment assay for gene targeting based on the polymerase chain reaction", Nucleic Acids Research, vol. 16, No. 18, IRL Press Limited, Oxford, England, 1988, 8887-8903.

Rajendrakumar et al., "DNA helix destabilization by proline and betaine: possible role in the salinitiy tolerance process", FEBS Letters, vol. 410, Federation of European Biochemical Sciences, 1977, 201-205.

Rees et al., "Betaine can eliminate the base pair composition dependence of DNA melting", Biochemistry, 993 [Abstract], 1993.

Schuchard et al., "Two-Step "Hot" PCR Amplification of GC-Rich Avian c-myc Sequences", BioTechniques, vol. 14, No. 3, 1993, 390-394.

Mouritzen et al., "Single Nucleotide Polymorphism Genotyping Using Locked Nucleic Acid (LNA™)," January, vol. 3, No. 1, pp. 27-38 (2003).

Extended European Search Report issued by the European Patent Office for Application No. 16784104.8, dated Feb. 12, 2019, 11 pages.

\* cited by examiner

Legend $y = 125.44 + 1.8224x$  $R^2 = 0.97052$

SEQUENCE LISTING

<160> NUMBER OF SEQ ID NOS: 25

<210> SEQ ID NO 1
<211> LENGTH: 40
<212> TYPE: DNA
<213> ORGANISM: Artificial

```
<220> FEATURE:
<223> OTHER INFORMATION: synthetic oligonucleotide

<400> SEQUENCE: 1
aagcttcagg tttagtacca gaacatgcag atgcttttaa                              40

<210> SEQ ID NO 2
<211> LENGTH: 41
<212> TYPE: DNA
<213> ORGANISM: Artificial
<220> FEATURE:
<223> OTHER INFORMATION: synthetic oligonucleotide

<400> SEQUENCE: 2
ttatctggga agaccatgta atcaaatttt cgtaagaatt c                            41

<210> SEQ ID NO 3
<211> LENGTH: 40
<212> TYPE: DNA
<213> ORGANISM: Artificial
<220> FEATURE:
<223> OTHER INFORMATION: synthetic oligonucleotide

<400> SEQUENCE: 3
ttcgaattac taaatcctgc agatacactc ccaccaatat                              40

<210> SEQ ID NO 4
<211> LENGTH: 33
<212> TYPE: RNA
<213> ORGANISM: B. anthracis
<220> FEATURE:
<221> NAME/KEY: misc_feature
<222> LOCATION: (1)..(33)
<223> OTHER INFORMATION: partial plcR mRNA sequence from GenBank
      accession number AY265698

<400> SEQUENCE: 4
aacauuuacg cugaaaaugg ccauuuuuaa gaa                                     33

<210> SEQ ID NO 5
<211> LENGTH: 29
<212> TYPE: RNA
<213> ORGANISM: B. anthracis
<220> FEATURE:
<221> NAME/KEY: misc_feature
<222> LOCATION: (1)..(29)
<223> OTHER INFORMATION: partial plcR mRNA sequence from GenBank
      accession number AY265698

<400> SEQUENCE: 5
caauacgaau aagcgcuuug ucaugcaaa                                          29

<210> SEQ ID NO 6
<211> LENGTH: 89
<212> TYPE: RNA
<213> ORGANISM: B. anthracis
<220> FEATURE:
<221> NAME/KEY: misc_feature
<222> LOCATION: (1)..(89)
<223> OTHER INFORMATION: partial plcR mRNA sequence from GenBank
      accession number AY265698 in the region represented by synthetic
      target dna R89

<400> SEQUENCE: 6
caaagcgcuu auucguauug auugccaag uauaaugcuu uugcaugauu augucucacc         60
uucacaucaa acucuuuauu aucauguaa                                          89
```

```
<210> SEQ ID NO 7
<211> LENGTH: 40
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (30)..(30)
<223> OTHER INFORMATION: U is modified with biotin
<220> FEATURE:
<221> NAME/KEY: misc_feature
<222> LOCATION: (35)..(35)
<223> OTHER INFORMATION: U is modified with biotin
<220> FEATURE:
<221> NAME/KEY: misc_feature
<222> LOCATION: (40)..(40)
<223> OTHER INFORMATION: U is modified with biotin

<400> SEQUENCE: 7
aggtgagaca taatcatgca tttttttttu ttttuttttu                         40

<210> SEQ ID NO 8
<211> LENGTH: 35
<212> TYPE: DNA
<213> ORGANISM: Artificial
<220> FEATURE:
<223> OTHER INFORMATION: synthetic oligonucleotide

<400> SEQUENCE: 8
gcaggattta gtaattcgaa tttttttttt ttttt                              35

<210> SEQ ID NO 9
<211> LENGTH: 35
<212> TYPE: DNA
<213> ORGANISM: Artificial
<220> FEATURE:
<223> OTHER INFORMATION: synthetic oligonucleotide

<400> SEQUENCE: 9
tggtactaaa cctgaagctt tttttttttt ttttt                              35

<210> SEQ ID NO 10
<211> LENGTH: 35
<212> TYPE: DNA
<213> ORGANISM: Artificial
<220> FEATURE:
<223> OTHER INFORMATION: synthetic oligonucleotide

<400> SEQUENCE: 10
tacatggtct tcccagataa tttttttttt ttttt                              35

<210> SEQ ID NO 11
<211> LENGTH: 44
<212> TYPE: DNA
<213> ORGANISM: Artificial
<220> FEATURE:
<223> OTHER INFORMATION: synthetic oligonucleotide

<400> SEQUENCE: 11
tttttttttt ttttttttca gaagaattct tacgaaaatt tgat                    44

<210> SEQ ID NO 12
<211> LENGTH: 41
<212> TYPE: DNA
<213> ORGANISM: Artificial
<220> FEATURE:
<223> OTHER INFORMATION: synthetic oligonucleotide
```

<400> SEQUENCE: 12
tttttttttt ttttttttctt tgatattggt gggagtgtat c        41

<210> SEQ ID NO 13
<211> LENGTH: 35
<212> TYPE: DNA
<213> ORGANISM: Artificial
<220> FEATURE:
<223> OTHER INFORMATION: synthetic oligonucleotide

<400> SEQUENCE: 13
tttttttttt tttttttaaa agcatctgca tgttc        35

<210> SEQ ID NO 14
<211> LENGTH: 40
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (30)..(30)
<223> OTHER INFORMATION: U is modified by biotin
<220> FEATURE:
<221> NAME/KEY: misc_feature
<222> LOCATION: (35)..(35)
<223> OTHER INFORMATION: U is modified by biotin
<220> FEATURE:
<221> NAME/KEY: misc_feature
<222> LOCATION: (40)..(40)
<223> OTHER INFORMATION: U is modified by biotin

<400> SEQUENCE: 14
aggtgagaca taatcatgca ttttttttu ttttuttttu        40

<210> SEQ ID NO 15
<211> LENGTH: 38
<212> TYPE: DNA
<213> ORGANISM: Artificial
<220> FEATURE:
<223> OTHER INFORMATION: synthetic oligonucleotide

<400> SEQUENCE: 15
aggtgagaca taatcatgca tttttttttt tttttttt        38

<210> SEQ ID NO 16
<211> LENGTH: 20
<212> TYPE: DNA
<213> ORGANISM: Artificial
<220> FEATURE:
<223> OTHER INFORMATION: synthetic oligonucleotide

<400> SEQUENCE: 16
aggtgagaca taatcatgca        20

<210> SEQ ID NO 17
<211> LENGTH: 20
<212> TYPE: DNA
<213> ORGANISM: Artificial
<220> FEATURE:
<223> OTHER INFORMATION: synthetic oligonucleotide

<400> SEQUENCE: 17
taataaagag tttgatgtga        20

```
<210> SEQ ID NO 18
<211> LENGTH: 20
<212> TYPE: DNA
<213> ORGANISM: Artificial
<220> FEATURE:
<223> OTHER INFORMATION: synthetic oligonucleotide

<400> SEQUENCE: 18
aagcattata cttggacaat                                               20

<210> SEQ ID NO 19
<211> LENGTH: 20
<212> TYPE: DNA
<213> ORGANISM: Artificial
<220> FEATURE:
<223> OTHER INFORMATION: synthetic oligonucleotide

<400> SEQUENCE: 19
tggacaatca atacgaataa                                               20

<210> SEQ ID NO 20
<211> LENGTH: 89
<212> TYPE: DNA
<213> ORGANISM: Artificial
<220> FEATURE:
<223> OTHER INFORMATION: synthetic oligonucleotide

<400> SEQUENCE: 20
caaagcgctt attcgtattg attgtccaag tataatgctt ttgcatgatt atgtctcacc   60
ttcacatcaa actctttatt atcatgtaa                                    89

<210> SEQ ID NO 21
<211> LENGTH: 179
<212> TYPE: RNA
<213> ORGANISM: Artificial
<220> FEATURE:
<223> OTHER INFORMATION: predicted in vitro transcription product

<400> SEQUENCE: 21
gggagauuug caugacaaag cgcuuauucg uauugauugu ccaaguauaa ugcuuuugca   60
ugauuauguc ucaccuucac aucaaacucu uuauuaucau guauacuuc uaauugcuuu   120 aauauauuuu cauauaacuc aauacucuuc uuaaaauggc cauuucagc guaaauguu   179

<210> SEQ ID NO 22
<211> LENGTH: 38
<212> TYPE: DNA
<213> ORGANISM: Artificial
<220> FEATURE:
<223> OTHER INFORMATION: synthetic oligonucleotide

<400> SEQUENCE: 22
gcggtcccaa aagggtcagt cgtagcacac cactttca                          38

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
ttattcgtat tgattgtcca                                               20
```

```
<210> SEQ ID NO 24
<211> LENGTH: 46
<212> TYPE: DNA
<213> ORGANISM: Artificial
<220> FEATURE:
<223> OTHER INFORMATION: synthetic oligonucleotide

<400> SEQUENCE: 24
ttctaatacg actcactata gggagatttg catgacaaag cgctta                          46

<210> SEQ ID NO 25
<211> LENGTH: 23
<212> TYPE: DNA
<213> ORGANISM: Artificial
<220> FEATURE:
<223> OTHER INFORMATION: synthetic oligonucleotide

<400> SEQUENCE: 25
aacatttacg ctgaaaatgg cca                                                   23
```

MINIATURIZED LATERAL FLOW DEVICE FOR RAPID AND SENSITIVE DETECTION OF PROTEINS OR NUCLEIC ACIDS

RELATED APPLICATIONS

This patent application is a continuation of U.S. patent application Ser. No. 15/012,804, entitled "Miniaturized Lateral Flow Device for Rapid and Sensitive Detection of Proteins or Nucleic Acids", filed Feb. 1, 2016, which is a continuation of U.S. patent application Ser. No. 11/894,910, entitled "Miniaturized Lateral Flow Device for Rapid and Sensitive Detection of Proteins or Nucleic Acids", filed Aug. 22, 2007, now abandoned, which claims the benefit of the filing date of U.S. Provisional Patent Application No. 60/839,537 filed Aug. 22, 2006 and U.S. Provisional Patent Application No. 60/925,210 filed Apr. 18, 2007 under 35 U.S.C. 119(e).

STATEMENT AS TO RIGHTS TO INVENTIONS MADE UNDER FEDERALLY SPONSORED RESEARCH OR DEVELOPMENT

This invention was made with government support under Contract No. DE-AC52-06NA25396, awarded by the United States Department of Energy. The government has certain rights in this invention.

REFERENCE TO A SEQUENCE LISTING, A TABLE, OR COMPUTER PROGRAM

Applicant hereby submits a sequence listing as a text file titled 10192-Cary-Seq-List-1_ST25.txt created on Feb. 13, 2017, having 17K kbytes that is ASCII compliant and is incorporated herein by reference.

BACKGROUND OF THE INVENTION

The threat presented by biological weapons, global health care issues and emerging diseases of natural origin lend urgency to the development of rapid, field-deployable pathogen detection and diagnostic tools (1, 2). Ideally, to be of general field utility, a diagnostic device must be capable of sensitive and specific pathogen detection while retaining simplicity of use and independence from complex laboratory instrumentation (3). Additional challenges are presented by the need to screen samples for multiple pathogenic or toxic agents, a characteristic highly desirable in cases where commonalities in early symptom presentation confound differential diagnoses.

While nucleic acid-based assays for pathogen detection and identification offer sensitivity, specificity and resolution, they are relatively elaborate and often costly, limiting their utility for point-of-care diagnostics and deployment under field conditions where a supporting laboratory infrastructure is limited or absent. Reliance upon polymerase chain reaction (PCR) and fluorescence detection of amplified nucleic acids has contributed significantly to the complexity and cost of nucleic acid diagnostics (2, 4-6). Retaining assay sensitivity, while circumventing requirements for thermocyclers and fluorescence detection hardware, remains a significant challenge.

The recent advent of DNA microarray technology has promised to increase the information capacity of nucleic acid diagnostics and enable the highly multiplexed detection of genetic signatures (7). The potential of DNA microarrays to detect, in parallel, large panels of distinct nucleic acid sequences has proven to be a powerful technique for many laboratory applications (for review see (8)). Nonetheless, the reliance of this technology on costly instrumentation for high-resolution fluorescence signal transduction severely limits the utility of microarrays for field applications where a laboratory infrastructure is limited or unavailable. Additionally, the long hybridization incubations required for microarray assays increase sample-to-answer times beyond what would be acceptable for a rapid screening assay. Though microarray hybridization times as short as 500 seconds have been reported (9), such methods employ relatively elaborate microfluidic designs that remain reliant upon fluorescent detection and do not address the need for low cost, easily manufactured devices that can be used without costly supporting instrumentation.

In contract to DNA-based assays, immunoassays have found widespread acceptance in low cost, easily used formats, perhaps the most notable of which is the chromatographic lateral flow immunoassay (for a review see (10)). Lateral flow assays, also known as hand-held assays or dipstick assays, are used for a broad range of applications where rapid antigen detection is required in an easily used, low cost format. Expanding the domain of lateral flow chromatography to nucleic acid detection, a number of recent reports have described lateral flow detection of PCR products using a variety of capture and detection schemes (11-14). Unfortunately, the utility of lateral flow detection in the context of a PCR-based assay is severely limited by the fact that reliance on thermocycling hardware largely negates the potential benefit of the otherwise highly simplified lateral flow platform. Additionally, a PCR-based approach to lateral flow detection necessitates each PCR reaction be subjected to post-amplification manipulations required to generate single-stranded products for hybridization-based detection.

Recent work has sought to alleviate reliance on PCR through employing isothermal nucleic acid amplification schemes or direct detection of unamplified genetic material. Enabled by the use of up-converting phosphor reporters, unamplified *Streptococcus pneumoniae* DNA sequence has been detected using a lateral flow assay format (15). Up-converting phosphor technology, while sensitive, remains dependent upon the hardware required to detect phosphor emission (16). The use of simple colorimetric detection schemes that circumvent the requirements for complex instrumentation require an upstream amplification strategy to attain suitable sensitivity. Isothermal nucleic acid amplification coupled with lateral flow detection has been reported for assays making use of cycling probe technology (CPT, (17)) and nucleic acid sequence-based amplification (NASBA, (18-20)) (21-25). While the work by Fong et al (21) made use of a lateral flow immuno-assay for DNA detection, the RNA Targets amplified by NASBA in the work from Baeumner's group (22-25) were detected using a lateral flow system enabled by the use of liposome encapsulated dye and a sandwich hybridization assay similar to that reported by Rule et al (12). While shown to display nanomolar sensitivity, the reported dye encapsulating liposome-based methods require additional washing steps and the liposomes are relatively labile, must be custom synthesized, and stored under stabilizing hydrated conditions (26).

SUMMARY OF THE INVENTION

The invention provides miniaturized lateral flow chromatographic and lateral flow chromatographic microarray devices (collectively, "LFM devices"), also termed "DNA dipstick", "nucleic acid dipstick", LFM dipstick" and "dipsick" devices, as well as diagnostic assay methods utilizing LFM technology and dipsticks and related diagnostic kits comprising LFM dipsticks.

The LFM technology and LFM devices of the invention offer many of the advantages of microarray technology yet retain the simplicity of lateral flow-based platforms. The miniaturization of lateral flow nucleic acid detection achieved by the present invention offers reduced reagent use, femtomole sensitivity, excellent linear dynamic range, and rapid detection. Moreover, the small feature sizes of capture oligonucleotides renders the potential information capacity of the platform comparable to more traditional spotted fluorescence microarrays as well as improving sensitivity. The LFM devices exemplified herein enable analytes to be detected within 10 seconds from the time of sample introduction to the LFM device. Sample volumes may be as low as about 10 microliters, significantly reducing assay costs and ameliorating reagent storage logistics. Additionally, the miniaturization of lateral flow opens the door to highly multiplexed assays, allowing many proteins or nucleic acids to be detected in a single assay.

Coupled with an isothermal amplification technique, LFM provides a facile means of rapidly detecting nucleic acid targets while circumventing hardware requirements for fluorescence detection and PCR thermocycling.

The power of LFM is demonstrated in the Examples, infra. More specifically, Example 8 illustrates the utility of the lateral flow microarray (LFM) approach for sensitive detection and discrimination of closely related microbial signatures when present as minority sequences in complex nucleic acid mixtures, using an assay based on the nonsense mutation in the plcR gene of *B. anthracis*, that is absent in the near phylogenetic neighbors *B. thuringiensis* and *B. cereus* (27, 28). The results demonstrate that LFMs, making use of stable detection reagents suitable for dry storage, can be used to detect as little as 250 amol analyte within 2 minutes of sample addition. The miniaturization of lateral flow detection decreases reagent consumption and sample-to-answer times while increasing the potential information capacity of the platform to enable the development of highly multiplexed nucleic acid detection assays.

In one aspect, the invention provides a lateral flow chromatographic device for detecting the presence of at least one single-stranded target nucleic acid analyte in a fluid sample, comprising a chromatographic test strip which comprises (a) a sample receiving zone for receiving an aliquot of the sample and for receiving a labeled detection oligonucleotide, which detection oligonucleotide comprises a sequence which is complementary to a first sequence of the target nucleic acid; and, (b) a capture zone in lateral flow contact with the sample receiving zone, said capture zone comprising a microporous membrane, onto which at least one capture oligonucleotide is immobilized at a feature size of 500 μm diameter or smaller, and which comprises a sequence which is complementary to a second sequence of the target nucleic acid. In some embodiments, the microporous membrane is 3 mm or less in width. The lateral flow chromatographic device may combine the sample receiving zone and the capture zone, such that they comprise a contiguous microporous membrane. The microporous membrane is a lateral flow compatible nitrocellulose membrane having a pore size of between 0.2 and 20 μm. The detection oligonucleotide is labeled with a detectable particle of between 0.02 and 1 μm in diameter, including without limitation, polystyrene microspheres, latex particles, nano-gold particles, colloidal gold particles, metal particles, magnetic particles, fluorescently detectable particles, and semiconductor nanocrystals. In some embodiments, the detection oligonucleotide comprises a first portion having a sequence complementary to a part of the target sequence and a second portion having a non-target specific sequence of at least 9 nucleotides, which second portion is adjacent to the label. The second portion may, for example, be a poly (A) or poly (T) sequence of at least 9 nucleotides.

In some embodiments, the first sequence and second sequence of the target nucleic acid are adjacent within 2 bases, in order to take advantage of "base stacking" hybridization stability.

In another aspect, the invention provides a lateral flow chromatographic device for detecting the presence of at least one single-stranded target nucleic acid analyte in a fluid sample, comprising a lateral flow matrix which defines a flow path and which comprises in series: (a) a sample receiving zone for receiving an aliquot of a fluid sample; (b) a labeling zone in lateral flow contact with said sample receiving zone, wherein the labeling zone comprises a porous material containing at least one detection oligonucleotide reversibly bound thereto, which detection oligonucleotide is complementary to a first sequence of the target nucleic acid and is coupled to a detectable label; and, (c) a capture zone in lateral flow contact with said labeling zone, said capture zone comprising a microporous membrane, onto which at least one capture oligonucleotide is immobilized at a feature size of 500 μm diameter or smaller. In some embodiments, the microporous membrane is 3 mm or less in width. The lateral flow chromatographic device may combine the sample receiving zone and the capture zone, such that they comprise a contiguous microporous membrane. The microporous membrane is a lateral flow compatible nitrocellulose membrane having a pore size of between 0.2 and 20 μm. The detection oligonucleotide is labeled with a detectable particle of between 0.02 and 1 μm in diameter, including without limitation, polystyrene microspheres, latex particles, nano-gold particles, colloidal gold particles, metal particles, magnetic particles, fluorescently detectable particles, and semi-conductor nanocrystals. In some embodiments, the detection oligonucleotide comprises a first portion having a sequence complementary to a part of the target sequence and a second portion having a non-target specific sequence of at least 9 nucleotides, which second portion is adjacent to the label. The second portion may, for example, be a poly (A) or poly (T) sequence of at least 9 nucleotides.

In some embodiments, the first sequence and second sequence of the target nucleic acid are adjacent within 2 bases, in order to take advantage of "base stacking" hybridization stability.

In another aspect, the invention provides an assay method of testing for the presence of a target nucleic acid in a liquid sample, comprising applying or contacting the liquid sample to the sample receiving zone of the lateral flow chromatographic device of the invention, allowing the sample to transport by capillary action through the capture zone, and detecting the presence or absence of the target nucleic acid by detecting the presence of the label at the relevant capture zone feature.

In another aspect, the invention provides a method for detecting the presence of a target nucleic acid in a biological sample, comprising: (a) providing a biological sample suspected of containing the target nucleic acid sequence; (b) releasing nucleic acid from the biological sample; (c) amplifying the target nucleic acid using nucleic acid sequence based amplification (NASBA) to generate a solution containing amplified single-stranded RNA complementary to the target nucleic acid, if present in the extracted DNA and/or RNA from the biological sample; and, (d) assaying for the presence of the complementary RNA target nucleic acid using the assay method above.

Figure 1:
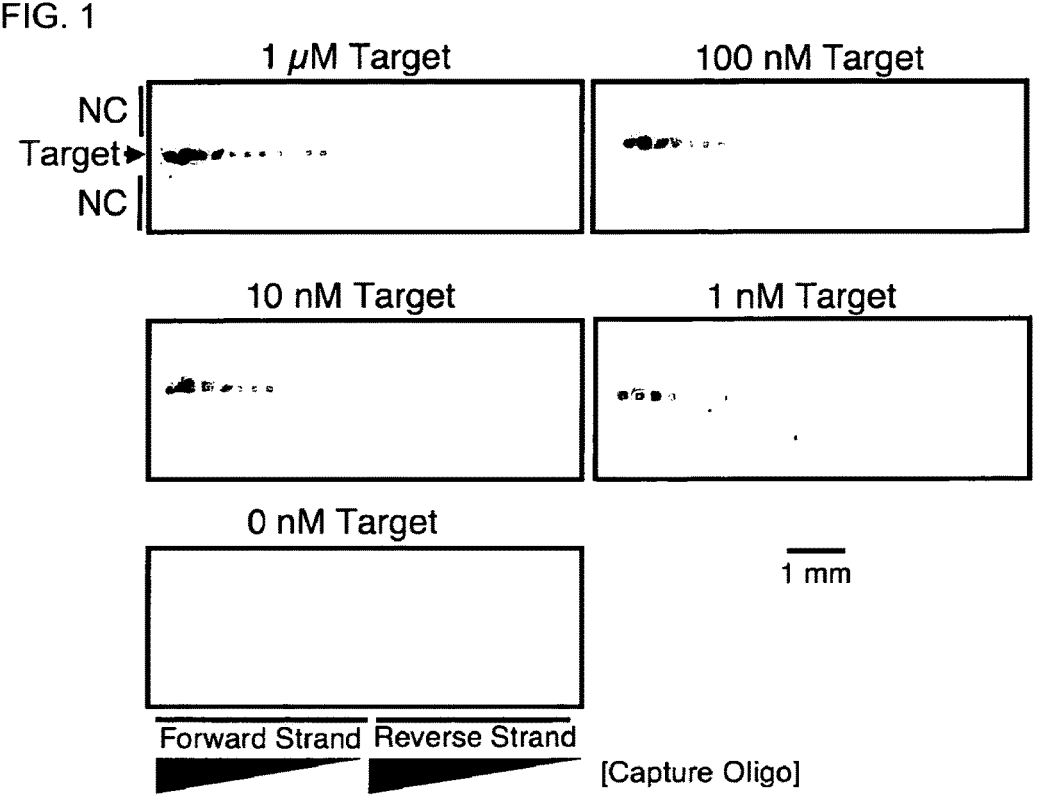
FIG. 1. Detection of DNA hybridization over range of capture oligonucleotide deposition concentrations on DNA dipstick. See Example 1.

LFM devices of the invention utilize sandwich-type hybridization, either employing sets of target-complementary oligonucleotides (or other nucleic acid molecules, such as dendrimers) to detect nucleic acid analytes, or binding ligands such as antibodies to detect protein analytes. In respect of nucleic acid detection methods using LFM, nucleic acid target is detected redundantly using (a) detectably labeled detection oligonucleotides complementary to one of two signature sequences on the target nucleic acid (i.e., oligonucleotides conjugated to a detectable label, such as dyed microspheres, semi-conductor nanocrystals, etc.), and (b) membrane-immobilized capture oligonucleotides complementary to the other signature sequence on the target. In the practice of a nucleic acid detection assay utilizing the LFM system of the invention, the capture of amplified target nucleic acids by the membrane-immobilized capture oligonucleotides and labeled detection oligonucleotides brings the label into contact with the membrane, displaying a visual or machine-readable optical signal. Thus, the assay requires positive hybridization to two distinct sequences on the target nucleic acid in order to produce a localized signal, resulting in very high assay specificity.

Physical Components of LFM Devices

The lateral flow chromatographic devices of the invention comprise a series of absorbent substrates which are used to transport analyte in a lateral manner to components containing certain reagents or materials required for the detection of the analyte.

In one aspect, a lateral flow chromatographic device of the invention comprises a chromatographic test strip which comprises (a) a sample receiving zone for receiving an aliquot of the sample and for receiving a labeled detection oligonucleotide, which detection oligonucleotide comprises a sequence which is complementary to a first sequence of the target nucleic acid; and, (b) a capture zone in lateral flow contact with the sample receiving zone, said capture zone comprising a microporous membrane, onto which at least one capture oligonucleotide is immobilized and which comprises a sequence which is complementary to a second sequence of the target nucleic acid. In an alternative embodiment, a labeling zone in lateral flow contact with said sample receiving zone is inserted up-stream of the capture zone and is lateral flow contact with the capture zone. A labeling zone comprises a porous material containing at least one detection oligonucleotide reversibly bound thereto, which detection oligonucleotide is complementary to a first sequence of the target nucleic acid and is coupled to a detectable label, thereby enabling the label step to take place on the device.

In a simplified illustration, one embodiment of the LFM device is structurally organized into at least 3 zones, comprising in linear orientation: (a) a sample pad constructed from absorbent material onto which a liquid, nucleic acid-containing sample is deposited, (b) a conjugate release pad containing a least one oligonucleotide-fitted detection particle (e.g., microsphere, bead, quantum dot), and (c) a detection zone comprising a nitrocellulose or nylon membrane containing at least one immobilized capture oligonucleotide. In some embodiments, a fourth element comprises an absorbent material which is capable of facilitating the lateral flow of the liquid sample from the sample pad end of the device to and through the detection zone. In some embodiments, the sample pad (a) and the conjugate release pad (b) are combined. In alternative embodiments, the conjugate release pad element is eliminated, and the sample to be assayed for the presence of a target nucleic acid is mixed with the oligonucleotide-fitted detection particle prior to placing the sample onto the sample pad.

The first substrate, or sample pad or sample receiving zone, comprises an absorbent material preferably composed of a matrix, with minimal nucleic acid binding properties, that will permit unobstructed migration of the nucleic acid analyte to subsequent stages of the apparatus without depletion. In a specific embodiment, the sample pad is composed of a cellulose fiber pad such as Millipore cellulose fiber sample pad material (Cat# CFSP223000).

In embodiments where separate sample and conjugate release pads are employed in the LFM device, the sample pad is situated within the device such that it is in physical contact with the conjugate release pad.

The substrate which contains the labeled detection oligonucleotide conjugate is termed the conjugate release pad or labeling zone. In some embodiments, the labeling zone is also used to receive sample directly. The conjugate release pad comprises a matrix composed of a material with minimal nucleic acid binding capacity and of a physical composition which allows dried detection particles to be liberated into solution with minimal residual binding to the matrix. Examples of materials suitable for conjugate pads include glass fiber and polyester materials (e.g., rayon). These materials are commonly available from various commercial sources (e.g., Millipore, Schleicher & Schuell).

The detection membrane of the capture zone may be any microporous membrane material which is lateral flow compatible, typically microporous cellulose or cellulose-derived materials such as nitrocellulose (e.g., HiFlow 135, Millipore) or nylon. In some embodiments, the sample receiving zone and the capture zone comprise a contiguous microporous membrane.

Typically, the microporous membrane defines a relatively narrow flow path. This may be achieved, for example, by utilizing narrow strips of microporous membrane material. Excellent results are obtained with membrane strips of 5 mm or less in width, with the best results being obtained with strips of 3 mm or less. As will be appreciated, other means for retaining a narrow flow path of less than 5 mm or less than mm may be used, and may include without limitation the use of barriers which define borders which limit the flow path to a channel.

The microporous membrane of the capture zone is a lateral flow compatible membrane such as cellulose, nitrocellulose, polyethersulfone, polyvinylidine fluoride, nylon, charge-modified nylon, and polytetrafluoroethylene. Typically, the membrane is nitrocellulose. The detection membrane is typically provided with a backing material for support, such as mylar or similar plastic materials. The membrane may be treated with agents that inhibit non-specific binding of analyte or other reagents used in an LFM assay.

In embodiments utilizing nitrocellulose, pore sizes typically range between 0.2 and 20 µm, and more typically between 0.2 and 12 µm. In preferred embodiments utilizing particle labels, the pore size of the microporous membrane should be on the order to about 10 times the diameter of the particle.

In one embodiment, the detection membrane is composed of a supported nitrocellulose membrane of sufficiently large pore structure to allow the unimpeded transport of detection reagent through the membrane matrix. Examples of suitable nitrocellulose materials for dyed microsphere mediated detection are Millipore HiFlow Plus HF09004, HF13504, Schleicher & Schuell Prima 60, Schleicher & Schuell Prima 85. The Millipore HF13504 nitrocellulose membrane has been demonstrated to provide rapid, specific and sensitive detection when patterned with appropriate capture oligonucleotides (see Examples, infra). The microporous membrane is placed in lateral flow contact with the labeling zone (conjugate release pad).

In some embodiments, an absorbent material is placed in lateral flow contact with the distal end of the detection membrane in order to facilitate lateral flow through the entire LFM device. Materials suitable for use as an absorbent pad include any absorbent material, including, but not limited to, nitrocellulose, cellulose esters, glass (e.g., borosilicate glass fiber), polyethersulfone, cotton, dehydrated polyacrylamide, silica gel, and polyethylene glycols. The rate of capillary flow can be controlled by choosing the appropriate absorbent zone material.

LFM devices may be encased in a housing as described in, e.g., U.S. Pat. No. 5,451,504. Materials for use in the housing include, but are not limited to, transparent tape, plastic film, plastic, glass, metal and the like. Such housings preferably contain an opening or sample port for introducing sample, as well as a window(s) permitting the visualization of the detection zone(s) of the detection membrane.

Microarray Fabrication:

In the fabrication of an LFM device, the microporous membrane of the capture zone is used for patterning capture oligonucleotides and or protein capture ligands (i.e., antibodies).

In preferred nucleic acid detection LFM fabrications, capture oligonucleotides are patterned onto the detection membrane or substrate (i.e., nitrocellulose) with spot diameter sizes ("feature sizes") of about 1 mm or less, preferably 600 µm or less, more preferably less than about 300 µm diameter, and in some embodiments, smaller (i.e., 50 to 200 µm, 50 to 250 µm, 50 to 300 µm). Oligonucleotide concentrations for spotting are generally in the range of 200 µM-800 µM. In embodiments in which PNAs or LNAs are used to synthesize oligonucleotides, lower densities may suffice.

Detection membranes may be patterned to suit the desired design of the detection element of the device. Methods for depositing nucleic acids and proteins onto microporous membranes such as nitrocellulose are well know, and negative and positive control reagents as well as capture reagents may be patterned on to the detection membrane using any of a number of deposition techniques. These techniques can be selected based on the density of information to be represented on the detection membrane. Manual deposition by pipette, automated deposition by robotics through contact mediated processes (stainless steel pins on a contact microarray printing robot) or noncontact mediated processes such as piezo responsive micropipettes, may all be used successfully to fabricate the nucleic acid detection device described here.

Preferably, when using nitrocellulose and similar membranes, non-contact printing techniques are used to deposit capture oligonucleotides or proteins onto the detection membrane, in order to retain the structural integrity of the detection membrane material. See. For example, the non-contact printing methods utilized in the Examples which follow.

Additionally, more convention means may be employed, including various techniques commonly used to fabricate hand held assay devices for the immunological detection of proteinaceous analytes in the context of a lateral flow immunochromatographic device.

For example, immobilization of capture oligonucleotides directly on the detection membrane may be accomplished by using high salt to adsorb the nucleic acid molecules to the surface of the membrane, combined with baking at about 80° C. to permanently fix the adsorbed oligonucleotides. Additionally, oligonucleotides may be deposited onto the membrane (i.e., nitrocellulose), air dried, and subjected to UV radiation (see Examples herein). Capture oligonucleotides may also be fixed directly to detection membrane by vacuum transfer in the presence of an equimolar concentration of sodium chloride and sodium citrate, or by the use of ultraviolet irradiation. The capture oligonucleotides may also be covalently linked to charge-modified nylon. In other embodiments, capture oligonucleotides may incorporate a reactive ligand (e.g., biotin) and may be immobilized indirectly on the detection membrane as a result of the interaction between the ligand and an immobilized member of a binding pair (e.g., streptavidin).

Detection membranes may be patterned with positive and negative control reagents and capture reagents in an array such that the physical position of each reagent is known. Positive control reagents can be composed of oligonucleotides complementary to detection oligonucleotides immobilized on detection reagents (i.e. dyed microspheres linked to oligonucleotides through a covalent bond or through an affinity interaction such as that mediated by streptavidin/biotin interactions). Alternatively, in embodiments where the streptavidin/biotin interaction is used to couple dyed microspheres to oligonucleotides the positive control array element can be composed of biotin in any of a number of forms suitable for immobilization on nitrocellulose (for example, a biotin labeled nucleic acid). Following binding to detection oligonucleotides, free biotin binding sites on streptavidin-conjugated dyed microspheres remain available for interaction with immobilized biotin on the detection membrane, thus providing one form of positive control.

Another positive control may be achieved by the immobilization of oligonucleotide on the detection membrane. The use of an oligonucleotide complementary to the dyed microsphere-conjugated detection oligonucleotide as a positive control allows direct hybridization of the detection oligonucleotide/dyed microsphere complex following lateral flow chromatography over the positive control. Negative controls for hybridization specificity can be incorporated into the device by patterning the detection membrane with detection oligonucleotide or other nucleic acid sequences predicted, by means known to those skilled in the art, to not hybridize to the detection oligonucleotide sequence.

For nucleic acid analytes, capture reagents are composed of oligonucleotides synthesized such that the sequence is complementary to a region of the analyte target nucleic acid not overlapping with the region complementary to the detection oligonucleotide. Ideally, the predicted secondary structure of the analyte target nucleic acid is examined to identify those regions exhibiting reduced likelihood of participating in intramolecular hydrogen bonds. Such regions are preferable sites for detection and capture oligonucleotide binding.

Array elements may take the form of lines, stripes, dots or human readable icons, letters or other forms or shapes deemed useful to the interpretation of device read-out. In the case of spots or dots deposited by robotic or manual means, individual feature sizes from 50 microns to 5 mm have been shown to provide accurate and interpretable hybridization mediated detection of 20 fmol analyte DNA molecules.

Capture and Detection Oligonucleotides:

For nucleic acid analytes, LFM devices incorporate two classes of oligonucleotide referred to here as capture and detection oligonucleotides. The detection oligonucleotide is linked by any of a number of means to a detection reagent or label that, when concentrated by capture through hybridization, renders the capture zone distinguishable (i.e., optically) from the surrounding substrate and from additional capture zones where the detection reagent has not been sequestered. Examples of detection reagents include polystyrene microspheres, latex particles, nano-gold particles, colloidal gold particles, metal particles, magnetic particles, fluorescently detectable particles, and semi-conductor nanocrystals and the like.

Alternatively, a nucleic acid complex, such as a DNA dendrimer or branched-DNA molecule, carrying multiple detectable moieties, such as fluorescent molecules or biotin, can be used to amplify lateral flow microarray signal intensity. By generating DNA dendrimers carrying a detection sequence complementary to a region of the target (detection sequence) each hybridization event at the LFM capture zone results in the localization of multiple detectable labels. Using a highly biotinylated dendrimer and a streptavidin conjugated detection particle such as a dyed microspheres or semi-conductor nanocrystals, both colorimetric and fluorescent signal amplification can be realized. For example, the large number of streptavidin binding sites on biotinylated dendrimers will increase the number of streptavidin bound particles captured by each hybridization event and generate a correspondingly amplified signal. Several potential advantages, especially with respect to multiplexed detection, may be realized using this approach. Specifically, the use of a generic biotin/streptavidin interaction allows the simultaneous use of multiple detection probe sequences without requiring the preparation of multiple quantum dot-detection probe conjugates. Together with the use of generic tag sequences added to amplicons through the use of specially designed NASBA primers, this approach is compatible with the development of generic tag-based LFMs suitable for the detection of differing panels of pathogens without redesign of the LFM layout.

The detection oligonucleotide is designed such that the melting temperature of the resulting oligonucleotide allows hybridization to its cognate sequence on the analyte under ambient conditions with sufficient rapidity to allow duplex formation to occur during lateral flow. Detection oligonucleotides with Tm of 50-70° C. have been shown to provide effective reagents for the detection of relevant analytes (using approximately 20-mer oligonucleotides).

Detection oligonucleotides are synthesized with suitable modifications to allow the efficient linkage to appropriate detection reagent. In some embodiments it is advantageous to include a spacer sequence consisting of 9 to 20 T residues proximal to the modified end of the oligonucleotide that will be coupled to the detection reagent. Chemistries of known suitability for use in the device include biotin/streptavidin through a biotin incorporated onto either the 5' or 3' end of the detection oligonucleotide and covalent cross-linking through a primary amine incorporated into either the 3' of 5' end of the detection oligonucleotide. In one preferred process, detection oligonucleotides are covalently linked to polystyrene microspheres using the coupling agent 1-etyl-3-(3-dimethylaminopropyl-diimide HCl (EDAC). Other methods that mediate the formation of a stable complex between the detection reagent and the detection oligonucleotide under assay conditions should also be suitable for use in the fabrication of the device.

The second class of oligonucleotide used in the device is the capture oligonucleotide. This reagent is immobilized on the microporous detection membrane through the use of standard methods for coupling nucleic acids to nitrocellulose or nylon, including without limitation drying followed by ultraviolet light cross-linking using 0.5 Joules UV. The capture oligonucleotide is designed such that the sequence is complementary to the analyte target nucleic acid at a region predicted to have little or no secondary structure. The length of the capture oligonucleotide is typically approximately 20 bases in length or of a length, to generate a predicted melting temperature of approximately 50-70° C.

In some embodiments it may be advantageous to add a spacer sequence consisting of 9 to 20 T residues.

Detection and capture oligonucleotides can be synthesized using well known DNA synthesis chemistries. The incorporation of modified nucleic acids such as PNA (peptide nucleic acid) or LNA (locked nucleic acid) may be useful for the enhanced hybridization properties of these DNA derivatives. The use of PNA or LNA moieties in the preparation of detection and/or capture oligonucleotides will be useful in manipulating the desired melting temperature, and so may allow shorter oligonucleotides to be employed for detection and/or capture where sequence constraints preclude longer DNA oligonucleotides.

In some embodiments, detection and capture oligonucleotides are designed to hybridize to target nucleic acid within 0, 1 or 2 bases of each other, in order to increase the stability of hybridization via the "base stacking" phenomenon. Base stacking has been reported to stabilize hybridization and allow efficient capture of dilute nucleic acids by hybridization (38-42). The data generated in Example 6, infra, demonstrates that detection and capture oligonucleotides which bind in tandem result in significantly higher hybridization signals.

Detection Modalities:

The detection zone (detection membrane) of the lateral flow device may comprise one or more capture oligonucleotides which are complementary to one or more target sequences. The capture oligonucleotides are stably affixed to the sample-exposed surface(s) of the microporous detection membrane using standard methodologies. Protein capture reagents may also be patterned onto the detection membrane using standard methods.

The LFM devices of the invention can make use of diverse detection modalities, including visual detection signals resulting from the capture and increased local concentration of an appropriate detection particle. The resulting colorimetric signal can be visualized by eye. Alternatively, for more quantitative and sensitive detection of signal, an electronic instrument capable of detecting colorimetric signals may be employed. Such instruments include standard flatbed scanners, dedicated lateral flow chromatographic strip readers (e.g. QuadScan, KGW Enterprises, Inc), or a simple CCD based devices fabricated for the detection of colorimetric signals such as those employed by commercially available immunochromatographic test strips (e.g. Clearblue Easy Digital Pregnancy Test).

Visualization by eye can be aided by the fabrication of the device in a manner that generates an easily recognized or interpreted shape on the dipstick surface. One example would be the patterning of an LFM with elements in a physical configuration that results in the appearance of a letter or symbol indicative of a positive or negative result (e.g. a "+" or "−" symbol).

Embodiments that employ fluorescent detection reagents such as fluorescent nanoparticles (e.g. Qdots, QuantumDots, Inc.) offer the potential increased sensitivity that results from the application of fluorescence detection technology. Such embodiments can be read using any of a number of ultraviolet light sources including hand held UV lamps, UV emitting LEDs, and light sources with sufficient emission in the UV to excite the nanoparticles. A simple filter can be used to enhance the visualization of nanoparticle fluorescence emissions. For example, a long pass filter with a cut off below the emission wavelength of the nanoparticle may be employed. In the case of excitation with a white light source, an additional filter to limit excitation to UVA and shorter wavelengths can be used (e.g., a 380 nm short pass filter).

The microporous detection membrane may contain capture oligonucleotides printed monolithically in order to produce virtually any colorimetric pattern that can be visualized by the unaided human eye, such as bands, letters, numbers, symbols, and the like. If the sample contains both the first and second target sequences, colored beads with hybridized detection oligonucleotide-target nucleic acid will then hybridize to the immobilized capture oligonucleotide, and thereafter remain stably immobilized to the membrane at that physical location. Such "low density" components of the detection zone may be used to provide a rapid indication of the presence of a target sequence or sequences in the sample, visualized only be the unaided eye.

In addition, the capture zone may contain one or more "high density" components, capable of providing high resolution detail of the signatures of the sequences present in the sample nucleic acid. For example, an array of a number of distinct second detection oligonucleotides may be deposited in distinct physical locations on the membrane (i.e., an array of spots), each of which detection oligonucleotide is specifically complementary to a distinct target sequence. Such high-density arrays may be used to interrogate the sample for genotype signature sequences and the like. These array components may be read by methods well known in the art, including by scanning and computer assisted densitometry, the use of CCD cameras, etc.

Assay devices of the invention comprising such low and high density detection zones are termed "dual-density" systems, assays and devices. The principal design element of such dual-density devices is the provision of two levels of information obtained from a single sample. The low density component provides instantaneous visual information indicative of the presence or absence of a first level target sequence, and may be used to provide fundamental diagnostic information, such as the presence of a nucleic acid sequence indicative of a virus or bacteria in the sample. Because this information is provided by a colored band or other shape or symbol, the user is able to identify the presence of a target immediately and without the use of any instrumentation whatsoever.

The high density components may be assayed using standard instrumentation at any time following the assay. For example, the device may be stored or shipped for high density array analysis using appropriate instrumentation and/or expertise. Thus, as an example, such dual-density devices may be used by a consumer patient for determining whether a body fluid sample contains an influenza virus. A positive result indicates the need for having the high density component of the device analyzed by specialized personnel, in order to determine the influenza strain, subtype, or genotype, for example. The consumer patient is able to use the device to determine the need for profession medical attention. The medical professional is able to analyze the same device for more specific diagnostic information.

LFM Nucleic Acid Assays:

In one aspect of the invention, an LFM assay is provided. LFM assays of the invention are useful for the specific detection of a target analyte, typically from a complex sample of interest, and generally comprise the steps of extracting analyte material (i.e., DNA, RNA, protein) from sample of interest, enriching for the analyte, and detecting the presence of the analyte using an LFM device populated with target-specific capture elements.

In one aspect, the invention provides a method of testing for the presence of a target nucleic acid in a liquid sample, comprising applying or contacting the liquid sample to the sample receiving zone a lateral flow chromatographic device of the invention, allowing the sample to transport by capillary action through the capture zone, and detecting the presence or absence of the target nucleic acid by detecting the presence of the label at the relevant capture zone feature.

Various DNA and RNA extraction methodologies are routine and well known in the art. Various kits for the efficient extraction of total nucleic acid, RNA or DNA are widely available from a number of commercial entities. Any of these methodologies and kits may be used to extract nucleic acid from a sample to assessed using the LFM assay.

Single-stranded RNA or DNA targets may be amplified directly, while double-stranded DNA targets generally are rendered single-stranded before amplification. Methods for rendering single-stranded DNA templates from a double-stranded DNA targets include without limitation heat penetration (i.e., 95° C. for 5 minutes) and chemical denaturation (i.e., sodium hydroxide, followed by neutralization). Another method for rendering amplifiable single-stranded DNA from double-stranded DNA involves enzymatic unwinding of the double-stranded DNA, using for example a DNA helicase, which can open-up portions of the DNA, permitting primer and polymerase access and binding (see Kornberg and Baker, 1992, DNA Replication, 2nd edn, New York: WH Freeman and Company; Caruthers and McKay, 2002, Helicase structure and mechanism. Curr Opin Struct Biol 12: 123-133).

As used herein, a "target sequence" is a nucleotide sequence within a target nucleic acid molecule which is to be amplified. Within the target sequence is a primer binding portion, to which primers are designed to hybridize in order to initiate DNA polymerization.

The selection of a particular target sequence for amplification will relate to the LFM assay objectives. For example, where amplification is aimed at identifying a particular strain of an organism, the target sequence should be one of the unique genetic signatures which differentiates that strain from others to which it may be related. In some cases, this may be a single defining sequence. In other cases, a combination of target sequences may be required to reliably identify and differentiate the organism. The selection of target sequences which impart specificity to assays utilizing amplified genetic material involves considerations well known in the art, including for example, unique pathogen-specific sequences, toxins genes, virulence factors or specific signature sequence combinations.

In the practice of the invention, single or multiple target sequences may be amplified in a single reaction using suitable, specific primer oligonucleotides. When multiple target sequences are to be amplified, primers must be designed to avoid possible nonspecific interactions as is well known.

Extracted nucleic acids may be purified prior to amplification. A number of column type DNA and RNA purification devices are commercially available and may be employed for this purpose. Various other techniques for purifying DNA and RNA may be employed, including without limitation, electrophoresis, gradient separation, affinity purification, etc.

LFM assays are useful for the detection of single stranded amplification products derived from samples of interest (i.e., clinical samples, environmental specimens, etc.). LFM is compatible for use with virtually any nucleic acid amplification method. In the context of the rapid, simplified and highly sensitive LFM assays of the invention, LFMs are particularly intended for use with isothermal amplification technologies. In one embodiment, extensively characterized herein by way of the several Examples which follow, the isothermal amplification NASBA is utilized. NASBA-amplified target nucleic acids are detected at very high specificity in a matter of seconds.

NASBA is an RNA amplification methodology that offers several advantages over other RNA amplification methods, including the absence of a reverse transcriptase step. NASBA is an isothermal reaction performed at 41° C., which obviates the need for a thermocycler and may facilitate the production of point-of-test devices. A single-stranded antisense RNA product is produced during NASBA, which can be directly hybridized by a probe sequence to accelerate post-amplification interrogation of the product. Additionally, selection criteria for NASBA primers are less stringent than with other amplification methods, allowing easier primer design in selected less-conserved regions of the gene. Furthermore, the amplification power of NASBA has been reported to be comparable to, or sometimes even higher than that of PCR.

In this connection, the invention provides a method for detecting the presence of a target nucleic acid in a biological sample, comprising: (a) providing a biological sample suspected of containing the target nucleic acid sequence; (b) releasing nucleic acid from the biological sample; (c) amplifying the target nucleic acid using nucleic acid sequence based amplification (NASBA) to generate a solution containing amplified single-stranded RNA complementary to the target nucleic acid, if present in the extracted DNA and/or RNA from the biological sample; and, (d) assaying for the presence of the complementary RNA target nucleic acid.

In the LFM assay progression, initially, and typically following extraction and amplification of target nucleic acid, a solution containing one or more target sequences to be detected by the device is introduced to the sample pad. This may be achieved by dipping the lateral flow device sample pad/sample receiving zone into the solution, or by dropping a quantity of the solution onto the sample pad/sample receiving zone of the lateral flow device. The device is sufficiently robust that the composition of the buffer solution carrying the target sequence(s) is not critical, however, several practical considerations are taken into account to assure compatibility of the buffer with the device. Most significantly, the ionic strength of the sample buffer must be such that precipitation or aggregation of the detection particles does not occur. Similarly, sufficient ionic strength of the buffer is required to support hybridization during lateral flow. Impregnation of the sample pad and/or conjugate release pad with Triton-X100, SDS, BSA, ficol, and/or polyvinyl pyrolidone, or introduction of these components to the sample buffer itself, can stabilize the detection particles and block non-specific interactions between the detection particles and the detection membrane. While a range of concentrations of these reagents can be used successfully, buffers of proven efficacy include 0.1% ficol, 0.1% BSA, 1% Triton X-100, and 150 mM NaCl. This particular buffer supports mono-disperse detection particle suspensions.

Additionally, buffers containing higher concentrations of Triton X-100 and SDS have been found to support higher ionic strength environments without detection particle aggregation and may be used to facilitate hybridization. For example, 3% Triton X-100, 0.1% SDS, 600 mM NaCl has been shown to support subnanomolar hybridization-based detection on the device.

Optimized buffer, reagent parameters and coupling protocols for LFM devices utilizing nitrocellulose detection membranes are presented in Example 5.

Once on the sample pad/sample receiving zone, the analyte solution flows from the proximal (sample) end towards the distal (detection) end of the device. In one embodiment, detection oligonucleotide-functionalized dyed microbeads are embedded into the conjugate release pad component of the device, preferably in lyophilized form, ready to be re-hydrated as the analyte solution travels into this area of the device. As the analyte solution moves across the conjugate release pad, the microbeads are rehydrated and are available for detection oligonucleotide hybridization to target sequences within the sample. Target sequences, when present, will become hybridized to the detection oligonucleotide and thus to the beads. This complex continues lateral flow migration to the detection membrane, where immobilized capture oligonucleotides hybridize to the target sequence, thus capturing the target sequence-bead complex.

The invention also provides lateral flow chromatographic microarray devices. In one aspect, for example, the invention provides a lateral flow microarray chromatographic device for detecting the presence or absence of a plurality of single-stranded target nucleic acids in one or more fluid samples, comprising a lateral flow matrix which defines a flow path and which comprises in series: (a) a sample receiving zone for receiving the fluid sample(s); (b) a labeling zone in lateral flow contact with said sample receiving zone, wherein the labeling zone comprises a porous material containing a plurality of different detection oligonucleotides reversibly bound thereto, which detection oligonucleotides are complementary to first sequences of a plurality of respective target nucleic acids and are coupled to detectable labels; and, (c) a capture zone in lateral flow contact with said labeling zone, said capture zone comprising a microporous membrane, at least a portion of which contains a plurality of different capture oligonucleotides immobilized thereto, which capture oligonucleotides are complementary to second sequences of a plurality of respective target nucleic acids, and wherein the different capture oligonucleotides are immobilized to the microporous membrane at a feature size of 300 μm or less in diameter.

Another aspect is drawn to lateral flow chromatographic microarray devices which eliminate the labeling zone. For example, the invention provides A lateral flow microarray chromatographic device for detecting the presence or absence of a plurality of target nucleic acids in one or more fluid samples, comprising a lateral flow matrix which defines a flow path and which comprises in series: (a) a sample receiving zone for receiving the fluid sample(s) and for receiving a plurality of different detection oligonucleotides, each of which detection oligonucleotides comprises a sequence which is complementary to a first sequence of a specific target nucleic acid and is labeled; and, (b) a capture zone in lateral flow contact with said labeling zone, said capture zone comprising a microporous membrane, at least a portion of which contains a plurality of different capture oligonucleotides immobilized thereto, each of which capture oligonucleotides comprises a sequence which is complementary to second sequence of the specific target nucleic acid, and wherein the different capture oligonucleotides are immobilized to the microporous membrane at a feature size of 300 μm or less in diameter.

Kits are also provided. In aspects in which the labeling zone is eliminated, thereby requiring the addition of a labeled detection oligonucleotide, the invention provides a kit for testing the presence of a target nucleic acid in a sample, comprising: (a) a lateral flow chromatographic device or lateral flow chromatographic microarray device of the invention, and (b) a labeled detection oligonucleotide complementary to a second sequence in the target nucleic acid.

LFM, LFM assays and LFM devices of the invention are further described by way of the following examples, none of which are intended to be limiting.

EXAMPLES

Example 1: Detection of DNA Hybridization Over Broad Range of Capture Oligonucleotide Deposition Concentrations on DNA Dipstick DNA dipstick microarrays were fabricated at a density of 36 features per mm² using varying concentrations of capture oligonucleotide, as indicated In FIG. 1. Printing solutions of capture oligonucleotide at 200 μM, 100 μM, 50 μM, 25 μM, 12.5 μM, 6.25 μM, and 3.125 μM were prepared and patterned on to lateral flow membranes. The resulting DNA dipstick microarrays were introduced to 100 μl of synthetic target DNA at the indicated concentration of 1 μM, 100 nM, 10 nM, 1 nM, and 0 nM corresponding to 100 pmol, 10 pmol, 1 pmol, 100 fmol, and 0 fmol target molecules respectively. Capture of 100 fmol target molecule was apparent at capture oligonucleotide printing concentrations as low as 12.5 μM (FIG. 1). However, the most sensitive detection was obtained at higher capture oligonucleotide printing concentrations of 200 μM. Subsequent DNA dipsticks and DNA dipstick microarrays were fabricated using 200 μM solutions of capture oligonucleotide. These data demonstrate that DNA dipstick microarrays provide robust hybridization based detection over an order of magnitude range of capture oligonucleotide deposition concentrations. This further suggests that fabrication of DNA dipstick microarrays will be relatively insensitive to variations in capture oligonucleotide concentration resulting from varying synthesis efficiencies.

Example 2: Detection of Single and Multiple SS-DNA Species

The following example demonstrates sensitive detection of single-stranded DNAs using hybridization-based capture and dyed-microsphere colorimetric detection.

Sequences derived from the *B. anthracis* pagA, capB and cya genes were used to demonstrate multiplexed detection. DNA Dipsticks were patterned with capture sequences for the detection of fragments of three key virulence factors of *B. anthracis*.

The capture sequences used were:

```
pagD:
                                        [SEQ ID NO: 7]
5'-GCAGGATTTAGTAATTCGAATTTTTTTTTTTTTTT-3';

cyaD908:
                                        [SEQ ID NO: 8]
5' TGGTACTAAACCTGAAGCTTTTTTTTTTTTTTTTT 3';
and capD:
                                        [SEQ ID NO: 9]
5'-TACATGGTCTTCCCAGATAATTTTTTTTTTTTTTT-3'.

0.35 μm dyed COOH microspheres (Spherotech,
Inc.) were coupled using EDAC and standard
protocols to:
for capB detection
                                       [SEQ ID NO: 10]
5' amine-C12-TTTTTTTTTTTTTTTTTCAGAAGAATTCT
TACGAAAATTTGAT 3', for pagA detection
                                       [SEQ ID NO: 11]
5' amine-C12-TTTTTTTTTTTTTTTTCTTTGATATTGGT
GGGAGTGTATC;
and for cya detection
                                       [SEQ ID NO: 12]
5' amine-C12-TTTTTTTTTTTTTTTTAAAAGCATCTGCA
TGTTC.
```

Figure 2:
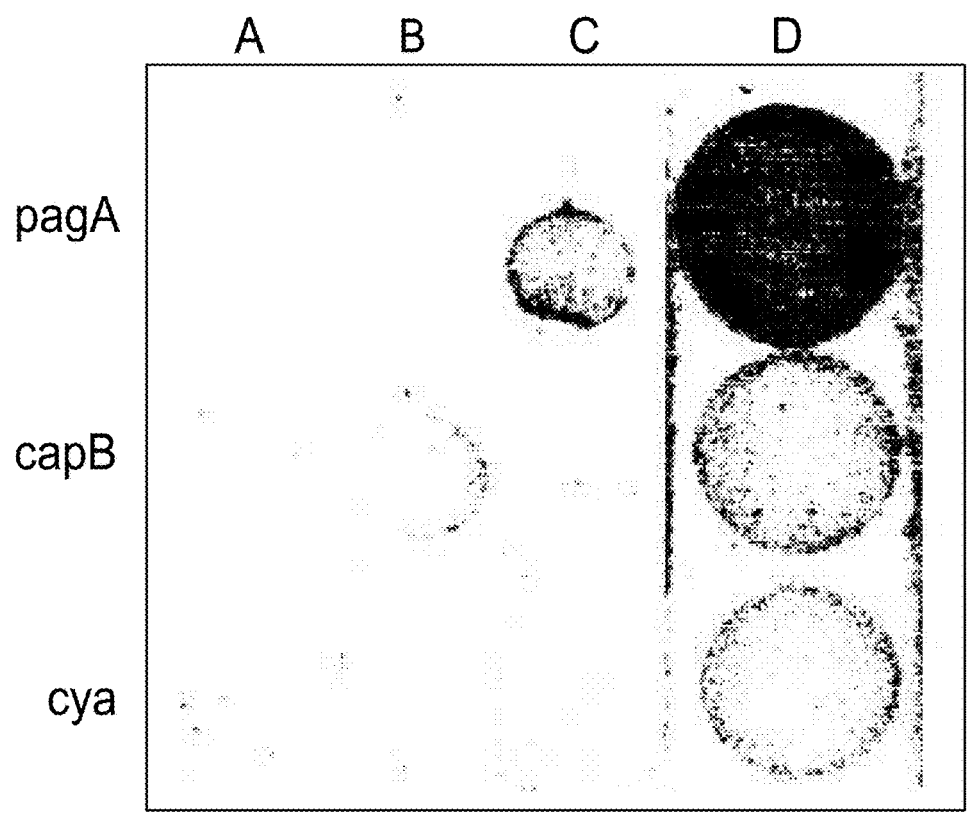
FIG. 2. See Example 2. (A) Dipstick exposed to 100 μl of sample containing 5 nM cya target sequence (i.e. 500 fmol target sequence) (5'-AAGCTTCAGGTTTAGTACCA-GAACATGCAGATGCTTTTAA-3') [SEQ ID NO: 1]. Signal is detectable as a blue dot only at the cya capture feature. (B) Dipstick exposed to 100 μl of sample containing 5 nM capB target sequence (5'-TTATCTGGGAAGACCATG-TAATCAAATTTTCGTAAGAATTC-3') [SEQ ID NO: 2]. Specific signal is generated at the cognate capB capture feature of the dipstick. (C) Dipstick exposed to 100 μl of sample containing 5 nM pagA target sequence (5'-TTC-GAATTACTAAATCCTGCAGATACACTCCCAC-CAATAT-3') [SEQ ID NO: 3]. Signal is detected only at the pagA capture site. In this particular dipstick, the negative results at the cya and capB capture sites can be visualized as faint white areas of microsphere exclusion at their respective capture positions. (D) Triplex dipstick detection of all three target sequences each present at a concentration of 5 nM in a 100 μl sample volume. For all panels, signal was visually discernible within 10 minutes.

Populations of beads coupled independently to these detection sequences were pooled for use as colorimetric labels in hybridization-based lateral flow detection assays. The results are shown in FIG. 2, and described in the description of FIG. 2. These data demonstrate rapid, specific and sensitive multiplexed hybridization-based detection in a lateral flow device.

Example 3: Sensitivity and Detection Time for DNA Dipstick and DNA Dipstick Microarray The sensitivity and time required to detect nucleic acids on DNA dipsticks and DNA dipstick microarrays were evaluated using synthetic target molecules for which exact concentrations could be determined.

Figure 3:
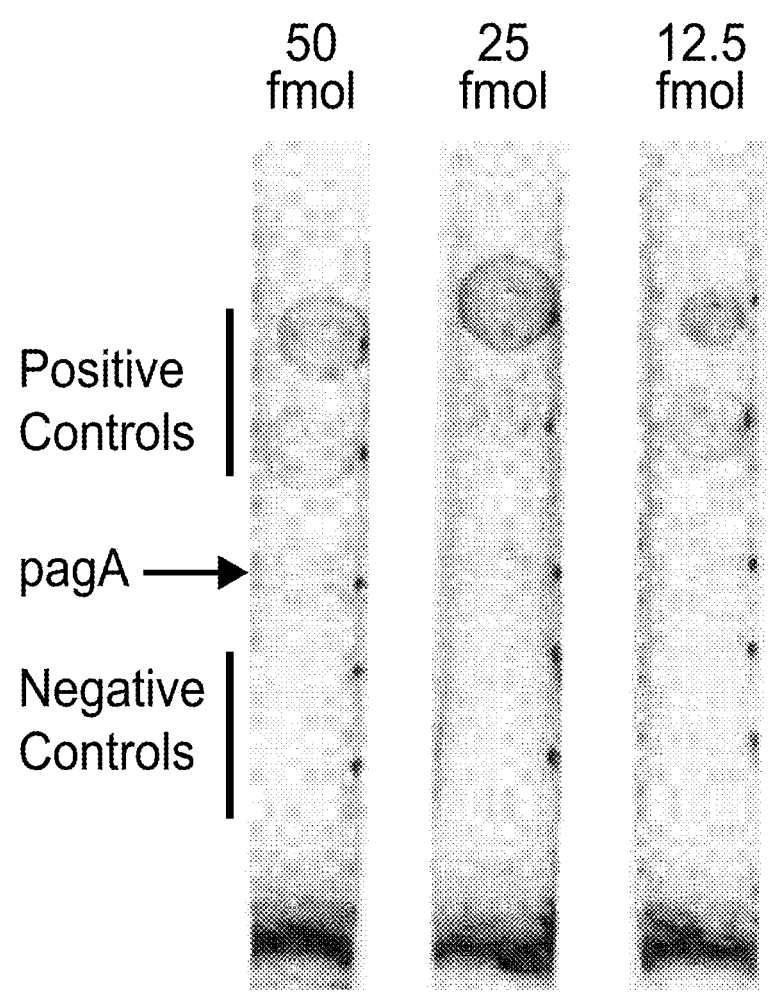
FIG. 3. Sensitivity and detection times for DNA dipstick and DNA dipstick microarrays. See Example 3.

Dipsticks were fabricated by manual deposition of capture oligonucleotides onto membrane strips of approximately 160 to 275 mm² surface area, features sizes were ~2-3 mm in diameter. Dipstick microarrays were printed using microarray fabrication robotics to pattern membrane strips of approximately 60 mm² surface area such that feature sizes were 300-600 μm in diameter. DNA dipsticks were challenged with 400 μl of synthetic target molecule in the presence of appropriate detection microspheres. Typical lateral flow time for these strips was approximately 45 minutes from sample introduction to complete transport of the sample through the dipstick matrix. Dilution series experiments revealed the sensitivity of detection to be 25 fmol (i.e. 400 µl of 62.5 µM target) (see FIG. 3).

Figure 4:
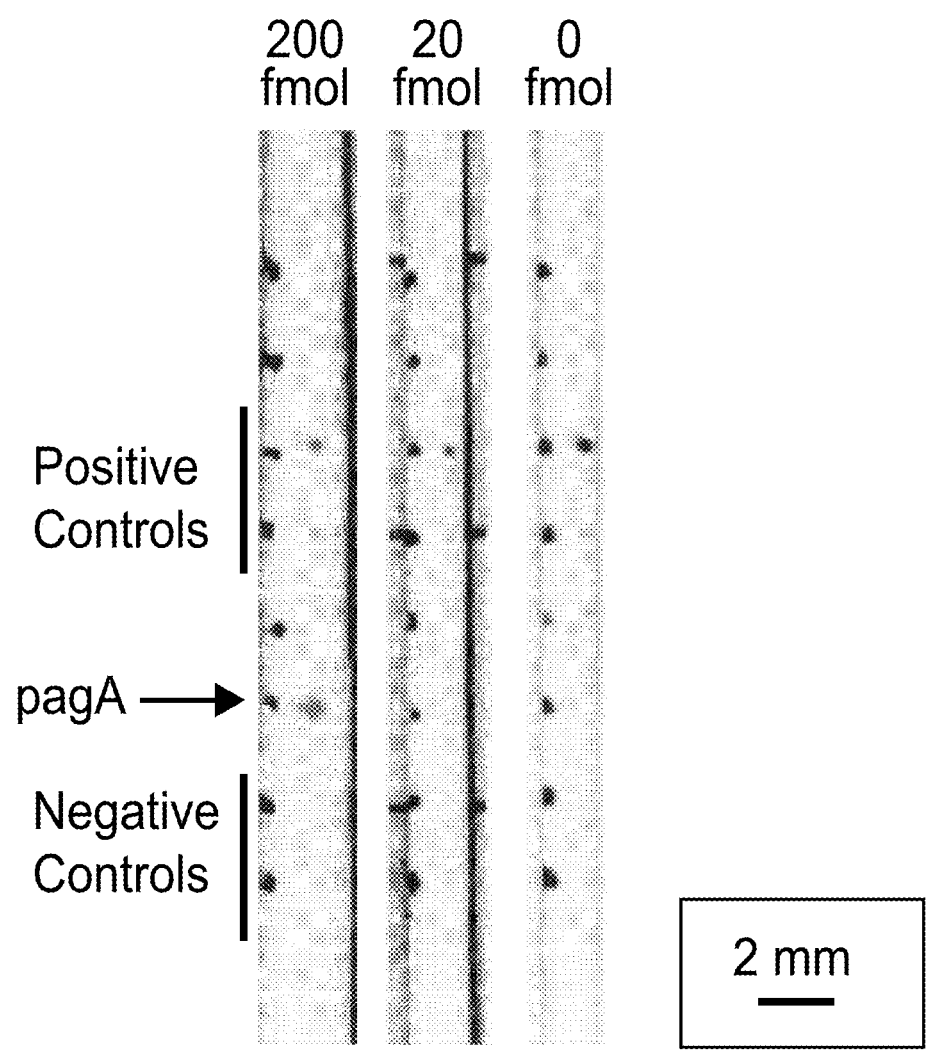
FIG. 4. Sensitivity and detection times for DNA dipstick microarrays, see Example 3.

To determine the effect of strip surface area and feature diameter on the speed and sensitivity of detection, lateral flow microarray strips were introduced to 10 µl of sample solution containing 20 nM, 2 nM and 0 mM target concentration (FIG. 4). Specific detection of the target was obtained within 1 minute. The sensitivity was found to be 20 fmol of target (i.e. detection of 2 nM target in 10 µl sample volume). The reduced surface area and sample volume result in more rapid detection than observed with dipsticks of more traditional size. Moreover, the sensitivity of the dipstick microarray was similar to that of the larger dipstick in terms of fmol detected. Thus, the DNA dipstick microarrays offer a more rapid detection platform with similar detection thresholds to those of larger strips while offering the increased information capacity inherent to high density microarray technology.

Example 4: Construction of Exemplary LFM Device

Figure 5:
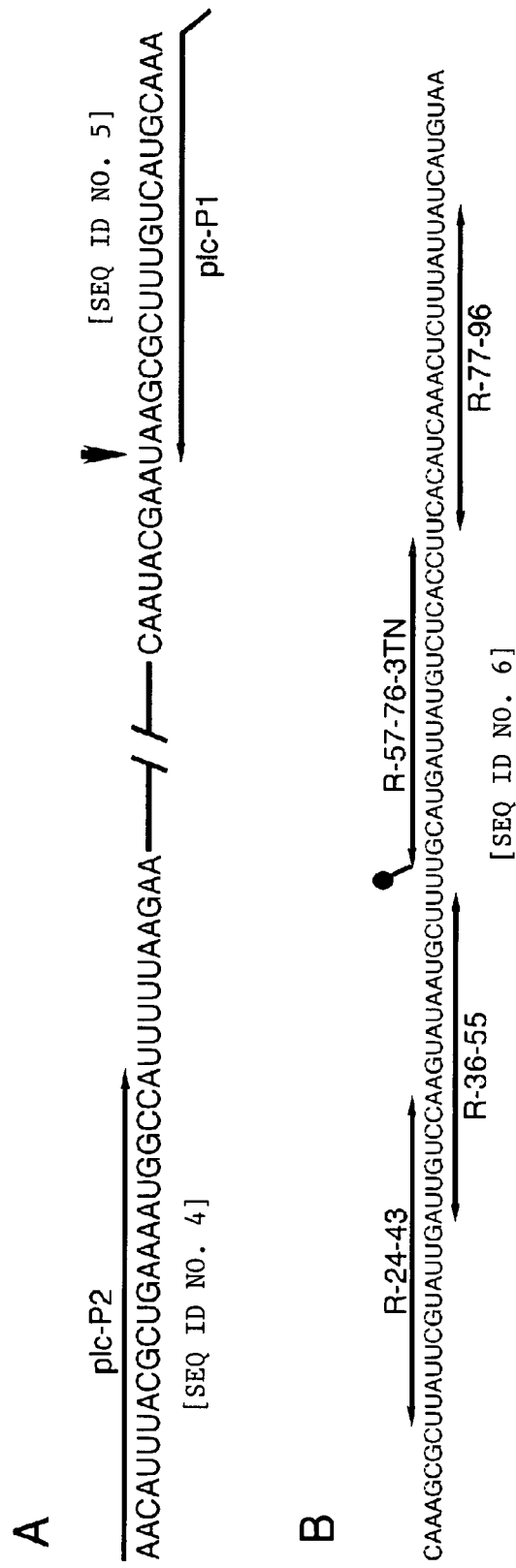
FIG. 5. (A) NASBA primer binding sites are shown in the relevant region of the predicted *B. anthracis* plcR mRNA sequence based on GenBank accession number AY265698 [SEQ ID NO: 4]. The terminal 3' base of plc-P1 is dnaR89 as a positive hybridization control, (−)R-57-76 as negative hybridization control, (24-43) capture probe R-24-43, (36-55) capture probe R-36-55, (77-96) capture probe R-77-96. (B) Graph of quantified signals from *B. anthracis* and *B. thuringiensis* challenged LFMs with linear regression line While the procedures used in Example 8 employed NASBA amplification and traditional RNA isolation protocols requiring approximately 90 minutes to complete, more recent advances in nucleic acid preparation and amplification have reported significant reduction in sample processing times (for a recent review see (47)). As amplification protocols become more rapid, the speed with which amplicons can be detected, without reliance on complex optical systems and fluorescent detection methods, will be critical to realizing the potential of these technologies. The LFM methods of the invention are able to achieve detection of nucleic acid analytes in less than 2 minutes. Given that 250 amol is equivalent to $1.5 \times 10^8$ molecules, efficient amplification methods that offer $10^9$ fold amplification, widely cited amplification levels for PCR- and NASBA-based techniques (22, 48), would theoretically enable the detection of single copy targets by LFM following amplification. Future systems that couple advanced amplification technologies and compatible streamlined nucleic acid preparation modalities with rapid LFM detection will allow significant decreases in sample-to-answer times without costly or complex instrumentation.
Figure 6:
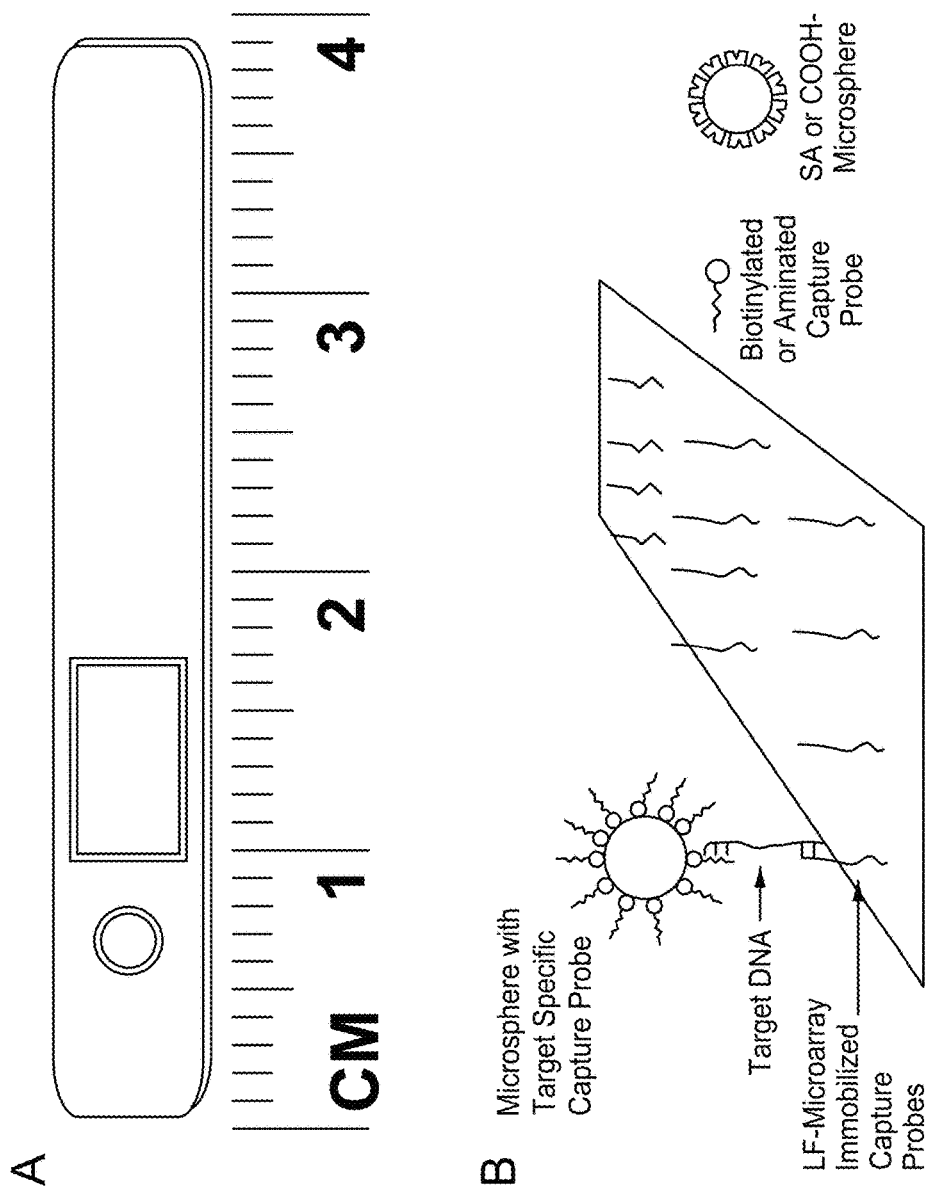
Figure 7:
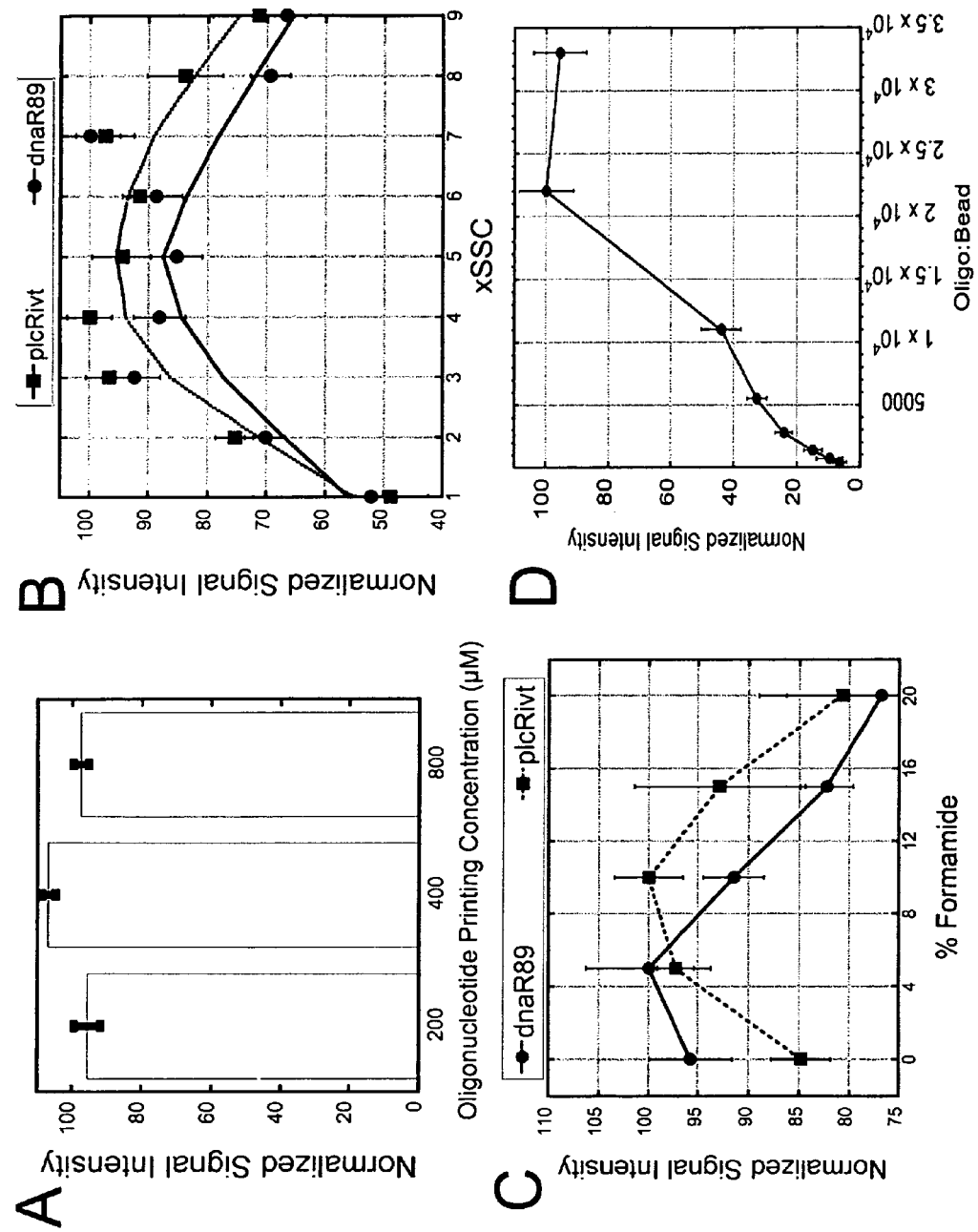

Materials and Methods:
LFM Fabrication:
Lateral flow microarrays (LFMs) were printed using a NanoPlotter 2.0 (GeSim, mbH, Dresden, Germany) non-contact picoliter deposition system equipped with NanoTips (GeSim). Unless otherwise indicated, LFMs were patterned with 400 µM solutions of oligonucleotide in $H_2O$ containing a 1:50 dilution of Ponceau S (P7767, Sigma) as a tracking dye. A lateral flow compatible nitrocellulose membrane (HiFlow 135, Millipore) was used as the LFM substrate. Following oligonucleotide deposition, nitrocellulose membranes were air dried and exposed to 5000 µJ UV in a StrataLinker (Stratagene). The resulting membrane sheets were cut into 3 mm wide, 30 mm long strips which were either used directly with buffer suspended dyed microspheres or assembled with conjugate release pads into a custom plastic housing. Housings were fabricated from polycarbonate sheet cut using a $CO_2$ laser (VersaLaser VL-300, Universal Laser Systems, Inc., Scottsdale, Ariz., USA). Conjugate release pads were made by impregnating glass fibre conjugate pad (GFCP203000, Millipore) with dyed microspheres covalently conjugated to R-57-76-3TN (see below) in 1% SDS. Microsphere saturated release pads were allowed to air dry under ambient conditions prior to assembly with LFM membranes.
Capture and Detection Oligonucleotides:
Table 1 provides capture and detection oligonucleotide sequences, their binding sites within the plcR amplicon are depicted in FIG. 5B. Amine modification and a $T_{18}$ spacer sequence were included on the 3' end of detection oligonucleotide R-57-76-3TN to allow covalent cross-linking to dyed microspheres and to facilitate hybridization in lateral flow sandwich assays respectively.
Conjugation of Detection Oligonucleotides to Dyed Microspheres:
SPHERO™ carboxyl-polystyrene 0.35 µm blue microspheres (Spherotech) were covalently conjugated to amino modified oligonucleotide R-57-76-3TN using the coupling agent 1-etyl-3-(3-dimethylaminopropyl-diimide HCl (EDAC, Pierce) under conditions adapted from Spiro et al (32). Briefly, $4 \times 10^{10}$ microspheres were suspended in 100 mM 2-(N-morpholino)ethanesulfonic acid pH 4.5 (MES, Sigma). Indicated amounts of oligonucleotide were introduced to MES suspended microspheres, vortexed and incubated in the presence of 0.5 mg/ml EDAC. Reactions were protected from light in aluminum foil wrapped tubes and incubated at room temperature for 30 min followed by the introduction of additional EDAC to bring the final EDAC concentration to 1 mg/ml. Incubation was continued for an additional 30 min after which beads were washed once with 1 ml 0.02% tween-20 (Sigma) and twice with 0.5 ml 0.1% SDS (Fisher Scientific). Beads were resuspended in 0.5 ml DNAase/RNAase free H2O. Bead suspensions were assessed for aggregation by phase-contrast light microscopy using a Zeiss IM135 inverted microscope.
Results:
Oligonucleotides for hybridization sandwich assays were designed to detect NASBA amplified *B. anthracis* plcR mRNA or synthetic targets based on relevant subregions of the plcR sequence. Oligonucleotides immobilized on the lateral flow substrate are referred to here as capture oligonucleotides while those conjugated to dyed microspheres for signal generation are referred to as detection oligonucleotides. Supported large pore nitrocellulose membranes were patterned with varying concentrations of capture oligonucleotides using a NanoPlotter™ 2.0 robotic positioning system (GeSiM, Groβerkmannsdorf, Germany) and NanoTip piezoelectronically actuated micropipets (GeSiM). Oligonucleotide dnaR89 was printed on LFM substrates as a positive hybridization control as this oligonucleotide carries sequence complementary to bead coupled detection oligonucleotide R-57-76-3TN. Negative hybridization controls included F-24-43 (the reverse complement of capture oligonucleotide R-24-43) and an unrelated sequence complementary to a region of the *F. tularensis* sdhA locus (FT-S18) (Pardington et al., submitted). By ejecting droplets from the micropipet at a distance of 500 μm from the nitrocellulose substrate, microarray feature sizes of approximately 200 μm could be generated. In contrast to contact microarray printing methods, this approach preserves the fragile pore structure of the membrane required for microsphere-based detection. Patterned nitrocellulose sheets were cut into 3 mm wide strips and then assembled with conjugate release pads in a custom designed plastic housing. An example of the resulting device is shown in FIG. 6A. Hybridization-mediated capture of analyte at the cognate capture element of the microarray and non-overlapping hybridization to dyed microsphere conjugated detection oligonucleotide generates a colorimetric signal arising from an increased local concentration of dyed microsphere particles. A schematic representation of the hybridization sandwich assay scheme is depicted in FIG. 6B.

Example 5: LFM Sandwich Hybridization Parameter Optimization

Materials and Methods:

LFM Fabrication:

LFMs were fabricated as described in Example 4, infra.

Detection and Capture Oligonucleotides:

Detection and capture oligonucleotides were designed as indicated in Example 4, infra. Conjugation of detection oligonucleotides to dyed, polystyrene microspheres was as described in Example 4.

Target Nucleic Acids:

A DNA oligonucleotide, dnaR89, composed of sequence derived from a region of the plcR gene of *B. anthracis*, as shown in FIG. 5B, was used to provide a readily available and quantifiable target for LFM assay development and optimization. The sequence of this synthetic target is provided in Table 1. Additionally, a full-length synthetic target RNA was generated by PCR followed by in vitro transcription. This RNA, referred to here as plcRivt, was used to confirm that reaction conditions established with dnaR89 were also suitable for the detection of NASBA reaction products. Synthesis of plcRivt was accomplished by using plc-P1 and plc-P2 primers in PCR reactions containing 20 ng of *B. anthracis* Stern strain 7702 genomic DNA. PCR reactions using Platinum PCR Supermix (Invitrogen) were conducted for 40 cycles of 94° C. for 30 s, 60° C. for 30 s and 72° C. for 1 min following an initial 2 min incubation at 94° C. The resulting amplicon was subjected to purification using QIAquick PCR clean-up spin-columns (QIAGEN) and subsequently used to program an in vitro transcription reaction using the T7 AmpliScribe kit (EpiCentre). The in vitro transcription reaction product was subjected to treatment with RNase free DNase I (Ambion) and purified using a RNeasy column (QIAGEN). The resulting RNA was quantified by measuring the $OD_{260}$. plcRivt is predicted to be identical in sequence to the NASBA product generated from *B. anthracis* total cellular RNA using plc-P1 and plc-P2.

Detection Protocol:

Following completion of sample flow, LFM membranes were allowed to air dry prior to scanning with a standard flatbed PC scanner (CanoScan 9950F, Canon, Inc.). Scans were performed at 2400 dpi resolution using 48 bit color. The resulting image files were converted to grayscale, inverted and saved as 16-bit TIFF files using Photoshop CS2 (Adobe). Image files were then analyzed using GenePix Pro 6.0 (Molecular Devices) to quantify microarray spot intensities for NASBA product detection and for dnaR89 dilution series experiments.

Results:

LFMs were fabricated using varying concentrations of capture oligonucleotide to determine optimum printing concentrations. Following lateral flow of 25 fmol dnaR89 in 4×SSC, 5% formamide, 1.4% Triton X-100, 0.1% SDS containing 0.5% R-57-76-3TN coupled microspheres LFMs were scanned on a flatbed scanner and the resulting images quantified. For all capture sequences examined, 400 μM oligonucleotide printing concentrations provided the most favorable signal intensity (FIG. 7A). Standard hybridization conditions employed for these and other characterization studies were determined through an iterative set of optimization experiments that examined the effects of ionic strength, formamide concentration and detection oligonucleotide to bead cross-linking ratios.

LFM Running Buffer Optimization:

Lateral flow running buffer was based on the widely used standard sodium citrate buffer (SSC) supplemented with 1.4% Triton X-100 and 0.1% SDS to reduce microsphere aggregation and 5% formamide to increase hybridization stringency and destabilize target secondary structure. Given the profound impact ionic strength has on the stringency of DNA hybridization (33, 34), SSC concentration was varied from 1× to 9× and assay performance evaluated by densitometry of lateral flow microarrays following hybridization sandwich assays conducted using 25 fmol of the synthetic target dnaR89 or approximately 200 fmol of plcRivt. FIG. 7B summarizes the results of SSC concentration optimization experiments. Near optimal signal intensity was obtained for both dnaR89 and plcRivt at SSC concentrations between 2× and 7×. 4×SSC was selected for use in standard LFM running buffer as it provided sensitive hybridization-based detection of plcR derived sequences and good capillary lateral flow characteristics.

To determine the optimum concentration of formamide in LFM running buffer, a series of LFM experiments were conducted at varying formamide concentrations using both dnaR89 and plcRivt. 10 μl of 4×SSC, 1.4% Triton X-100 and 0.1% SDS containing 25 fmol dnaR89 or approximately 200 fmol plcRivt and varying concentrations of formamide, as indicated in FIG. 7C, were subjected to LFM analysis and the resulting hybridization signals quantified by densitometry. These experiments revealed a slight but reproducible increase in signal intensity at 5% formamide. All subsequent studies presented here were performed using 4×SSC, 1.4% Triton X-100, 0.1% SDS, and 5% formamide.

Optimization of Oligonucleotide-Detection Microsphere Coupling:

Given that higher stock concentrations of synthetic oligonucleotide dnaR89 could be obtained which allowed high confidence quantification of this synthetic target relative to what could be achieved with comparatively dilute solutions of the in vitro transcription product plcRivt, subsequent LFM characterization studies made use of dnaR89. The similarity of buffer optima displayed dnaR89 and plcRivt synthetic targets supported the assertion that dnaR89 could be used as an accurate proxy for the performance of LFM assays for NASBA product detection. Others have reported similar findings concluding that appropriately designed DNA oligonucleotides can be used as synthetic targets for the development of assays ultimately used for NASBA product detection (35). Therefore, subsequent LFM assay optimization and characterization was conducted using dnaR89.

To determine the optimum ratios for cross-linking detection oligonucleotides to dyed polystyrene microspheres, we examined populations of beads coupled to oligonucleotide at varying ratios. The 3' amine modified detection oligonucleotide R-57-76-3TN was covalently linked to polystyrene dyed microspheres using EDAC. The resulting bead/oligonucleotide complexes were evaluated for their ability to mediate detection of dnaR89 in a hybridization sandwich assay. Coupling reactions using a $2.2\times10^4$:1 oligonucleotide to bead ratio were found to provide optimum signal as determined by densitometry (FIG. 7D).

Example 6: Characterization of LFM Assay Detection Sensitivity

Materials and Methods:

LMF fabrication, oligonucleotide conjugation protocols, target nucleic acids and detection protocols were as described in Examples 4 and 5, supra.

Variable Detection Oligonucleotides:

Detection oligonucleotide R-57-76-3TN carrying a 3' spacer region consisting of 18 T residues was compared to detection oligonucleotide R-57-76-3N, carrying the same analyte complementary sequence as R-57-76-3TN but without the $T_{18}$ spacer, in order to evaluate whether the poly-T spacer influences accessibility of microsphere-coupled detection oligonucleotides to their hybridization targets.

Variable Capture Oligonucleotides:

To determine the relative performance of hybridization sandwich assays making use of capture oligonucleotides with complementarity to different locations of the target sequence, three capture oligonucleotides were synthesized and compared using sandwich assays employing detection oligonucleotide R-57-76-3TN coupled dyed microspheres. R-77-96 was designed to participate in base stacking with R-57-76-3TN when hybridized to the target. Base stacking has been reported to stabilize hybridization and allow efficient capture of dilute nucleic acids by hybridization (38-42). The binding sites for the three capture oligonucleotides examined (R-77-96, R-36-55, and R-24-43) are illustrated in FIG. 5B. Varying quantities of synthetic target dnaR89, between 0 and 200 fmol, were used for these studies.

Results:

Detection Oligonucleotide Spacer Improves Hybridization Efficiency:

The detection oligonucleotide R-57-76-3TN carried a 3' spacer region consisting of 18 T residues to increase the accessibility of bead bound oligonucleotides for hybridization. R-57-76-3N, which carried the same analyte complementary sequence as R-57-76-3TN but without the $T_{18}$ spacer, was found to exhibit significantly reduced hybridization to dnaR89 consistent with prior reports that a poly (dT) spacer sequence increases hybridization efficiency to solid-phase coupled oligonucleotides (36, 37). $T_{18}$ spacers were not incorporated into LFM immobilized capture oligonucleotides as they were found to be dispensable for hybridization.

Figure 8:
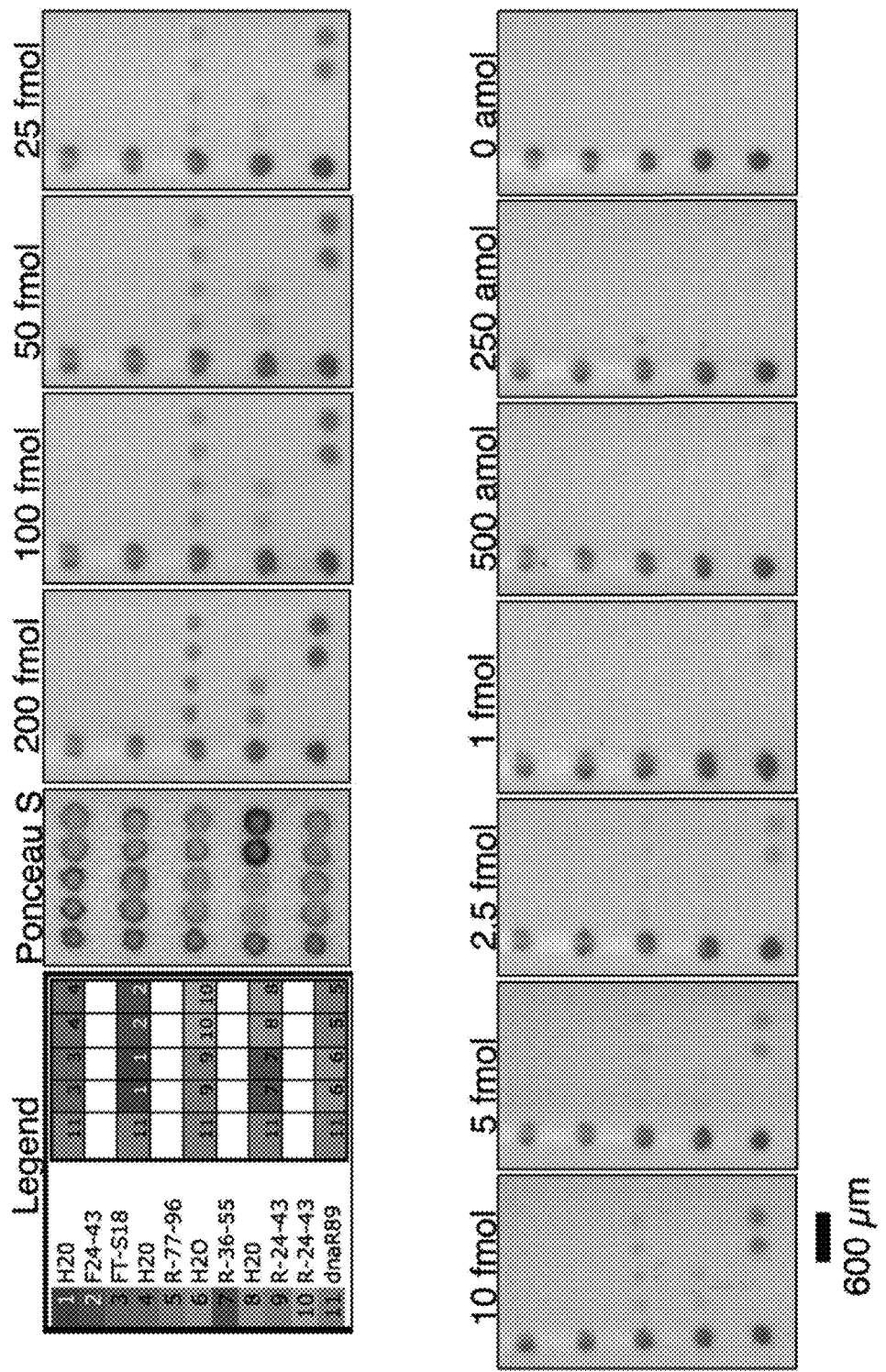

FIG. 8 depicts LFM membranes following detection of the indicated amounts of target oligonucleotide dnaR89. Images were collected using a flatbed scanner at 2400 dpi optical resolution, 48-bit color. LFMs carried dnaR89, which hybridizes directly to the microsphere conjugated detection probe, as a positive hybridization control. Positive control features were printed as the left most element of each LFM row to assist in feature identification. Negative hybridization controls, F24-43 and FT-S18, were based on the reverse complement of R-77-96 and an unrelated *F. tularensis* derived sequence respectively. Additionally, to confirm that no carryover contamination occurred during printing, $H_2O$ containing Ponceau S was printed on LFM substrates between positive control and capture oligonucleotide deposition. No signal was detectable in either hybridization negative controls or $H_2O$ negative control microarray elements.

Base Stacking Effect:

Background corrected signal intensity was determined from LFM images using GenePix Pro 6.0 microarray data extraction software. The results, presented in FIG. 9A, reveal R77-96 produces significantly higher hybridization signals than R-36-55 or R-24-43 for all examined quantities of dnaR89, suggesting a significant contribution of base stacking effects to LFM hybridization sandwich assay sensitivity.

Figure 9:
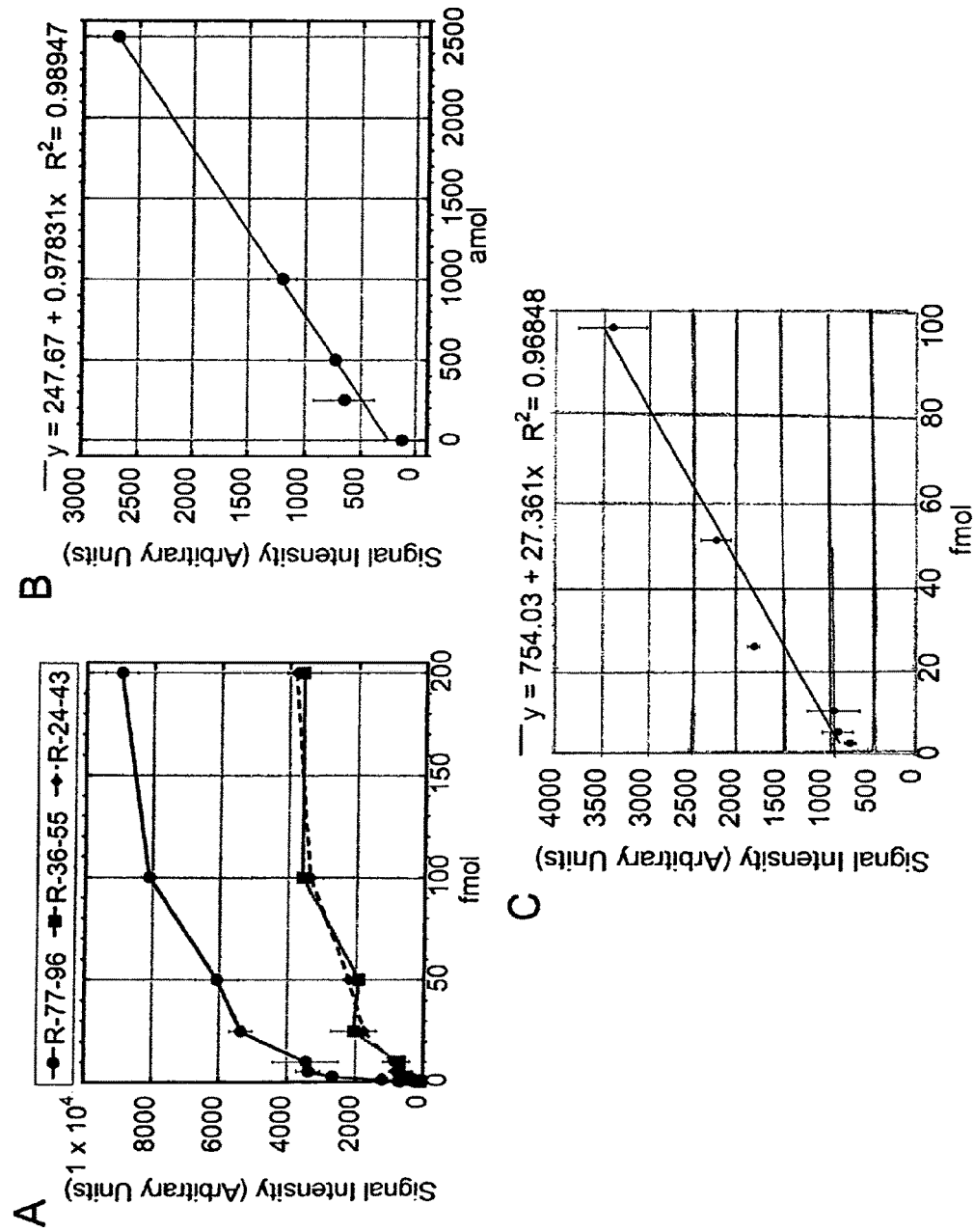

LFM Detection Sensitivity:

To define the detection limit of the LFM assay, a one-tailed t-test was used to determine quantities of dnaR89 that generated signal intensities significantly above 0 amol negative controls. Signals generated at R-77-96 capture features with 250 amol and greater quantities of dnaR89 were significantly higher than 0 amol dnaR89 controls ($p<0.05$, $n=6$). By the same criterion, 1 fmol dnaR89 detection limits were obtained for both R-24-43 and R-36-55 ($p<0.05$, $n=6$). FIG. 9B depicts the performance of LFM detection over the 0 to 2500 amol dnaR89 range using the R-77-96/R-57-76-3TN capture/detection probes. LFM detection exhibited excellent linearity, $R^2=0.989$, over this 10 fold range of target molecules. While capture probe R-24-43 exhibited less sensitivity than R-77-96, this capture probe displayed excellent signal linearity between 2.5 fmol and 100 fmol dnaR89, $R^2=0.968$ (FIG. 9C). These findings demonstrate that the LFM capacity to display multiple capture sequences can be used to simultaneously provide sensitive detection and extend assay linearity through the use of capture probes with differing hybridization characteristics.

Example 7: LFM Assay Time Course Evaluation

Materials and Methods:

LMF fabrication, oligonucleotide conjugation protocols, target nucleic acids and detection protocols were as described in Examples 4 and 5, supra.

For these time course studies, LFM assays were recorded using a digital video recorder (DCR-PC1, Sony). Video frames were collected for quantification using iMovie (Apple Computer). Feature intensity was quantified for time course studies and some optimization experiments using uncalibrated optical density in ImageJ (http://rsb.info.nih.gov/ij/). For better reproduction contrast, LFM images used for figures were cropped and modified by applying the Auto Contrast function in Photoshop CS2. No other modifications were applied.

Figure 10:
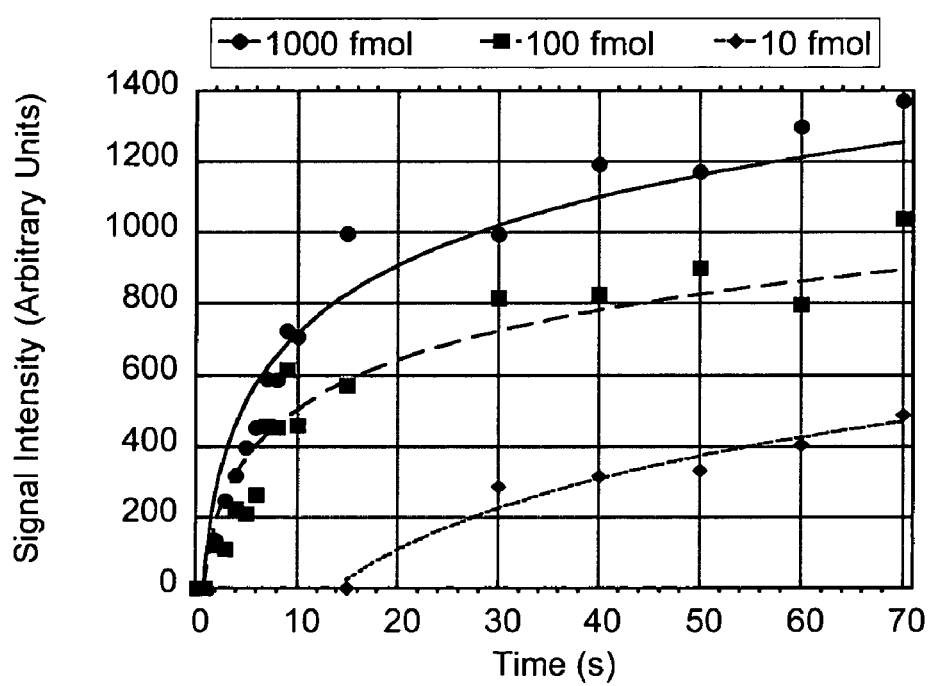
Figure 12:
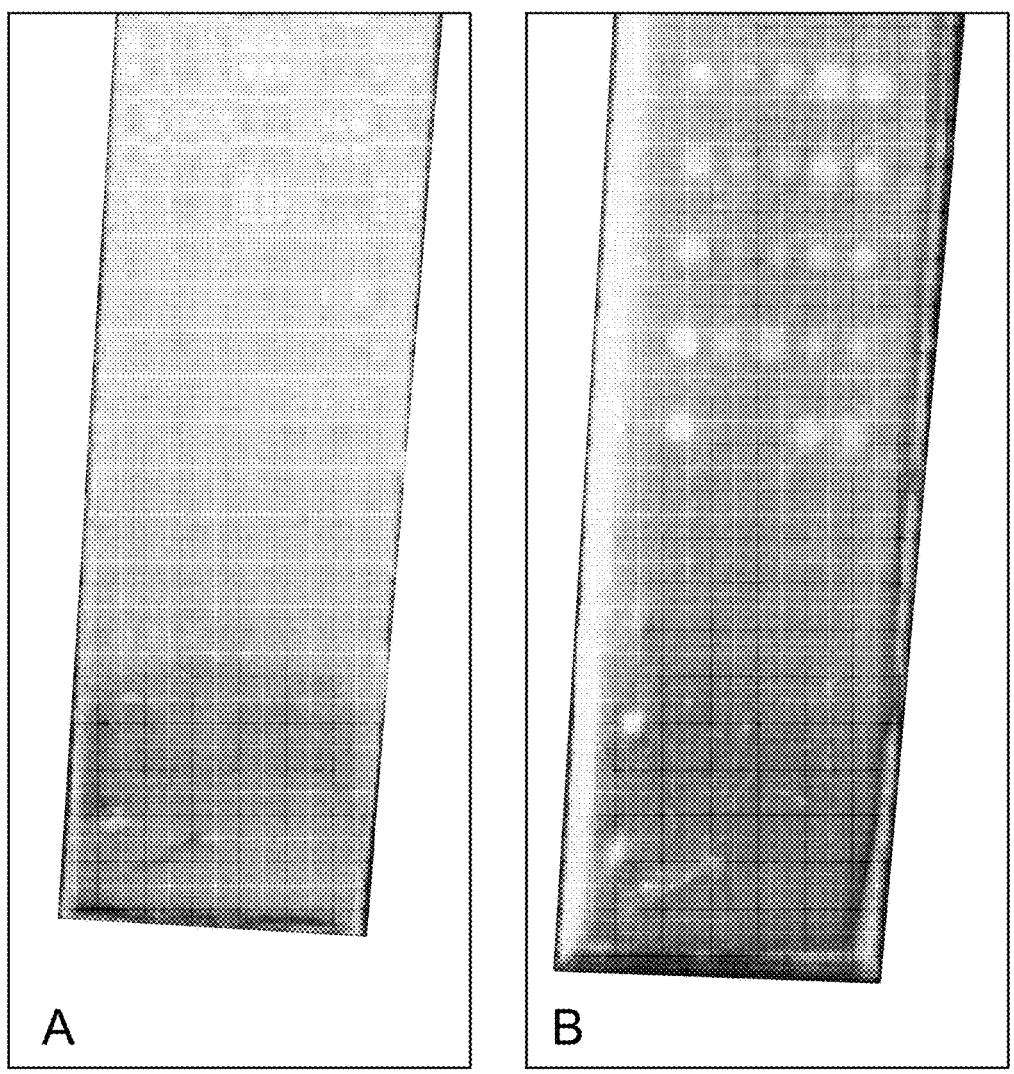
Figure 13:
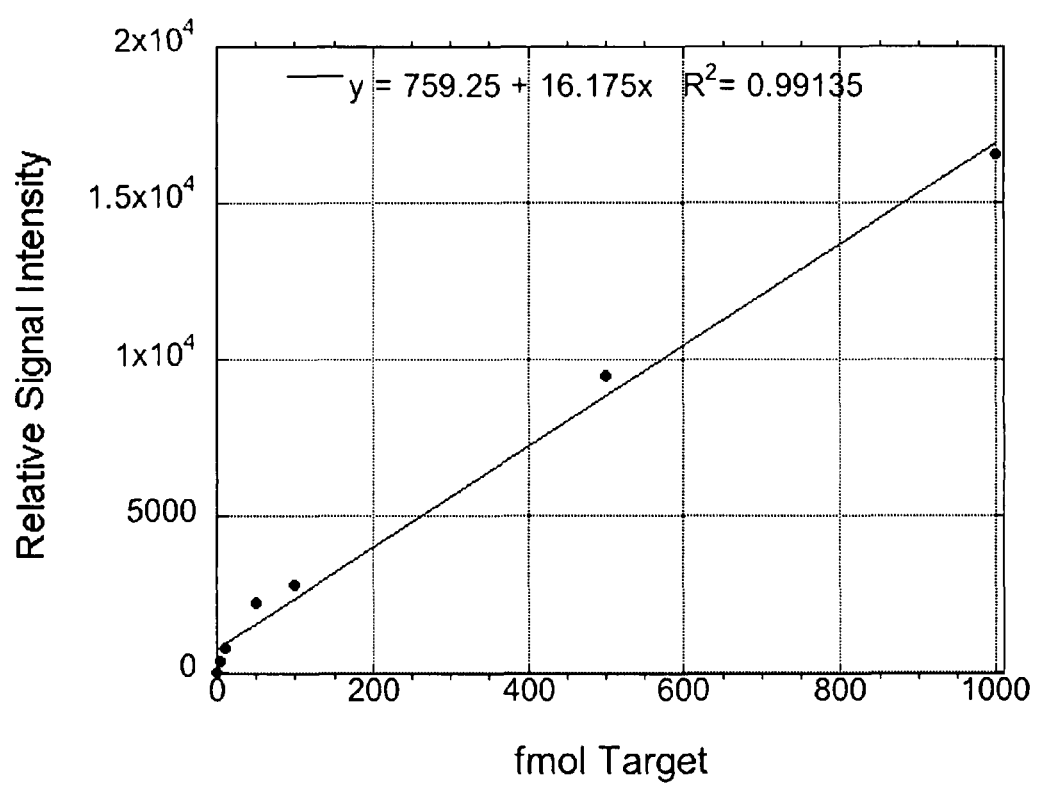

Results:

The small sample volumes used for LFM detection and the reduced surface area traversed during capillary lateral flow significantly reduces detection times for the LFM relative to traditional lateral flow devices. To quantitatively present the speed of LFM-mediated nucleic acid detection, we used digital video to follow hybridization sandwich assay mediated detection of synthetic target molecule dnaR89. These studies were conducted over a range of target concentrations using 10 µl of LFM running buffer containing suspended R-57-76-3TN conjugated dyed microspheres. Individual frames were isolated from video data sets and quantified for relative signal intensity over the course of capillary lateral flow across the LFM substrate. The resulting signal data was plotted versus time in seconds as shown in FIG. 10. For time measurements, $t_0$ was defined as the time when the sample front reached the first row of LFM features. Signal was detectable for 1000 fmol target in 2 seconds following sample transport across R-77-96 capture elements. 100 fmol dnaR89 was detectable within 4 seconds while 10 fmol was clearly detectable by 30 seconds as defined by the earliest time point at which 90% of the pixels composing the R-77-96 microarray features were greater than one standard deviation above background. Lateral flow transport of the 10 µl sample was complete by 120 seconds.

Example 8: LFM Assay for Detection of *Bacillus anthracis*

Materials and Methods:

LMF fabrication, oligonucleotide conjugation protocols, target nucleic acids and detection protocols were as described in Examples 4 and 5, supra. Table 1 provides capture and detection oligonucleotide sequences; binding sites within the plcR amplicon are depicted in FIG. 5B. Amine modification and a $T_{18}$ spacer sequence were included on the 3' end of detection oligonucleotide R-57-76-3TN to allow covalent cross-linking to dyed microspheres and to facilitate hybridization in lateral flow sandwich assays respectively.

RNA Isolation:

Total RNA was isolated from *B. anthracis* strain Sterne 7702 and *B. thuringiensis* strain HD 621 (29) using a previously reported protocol (30). Purified RNA was quantified by measuring $OD_{260}$ and evaluated by gel electrophoresis. $3\times10^8$ cells were used for RNA isolation typically yielding 50-75 µg of total RNA.

Amplification Primer Design

Nucleic acid sequence based amplification (NASBA, (20)) primers, plc-P1 and plc-P2, were designed to amplify a fragment of the plcR locus from *B. anthracis*. Primer sequences used for NASBA reactions are provided in Table 1, the T7 promoter sequence is italicized in plc-P1. Plc-P1 hybridizes to the plcR transcript such that the 3' end of the primer forms a base pair with the previously reported polymorphism strictly associated with *B. anthracis* (27, 28). The NASBA P2 primer, plc-P2, is located such that the amplified RNA resulting from NASBA is 179 bases in length, see FIG. 5A. Previously reported plcR-based *B. anthracis* real-time PCR assays (27, 28) have made use of an alternate upstream primer that generates a 83 bp product but may be poorly suited for NASBA given the optimal NASBA product size of 120-250 bases (31).

Nucleic Acid Sequence-Based Amplification (NASBA)

NASBA reactions were prepared according to the manufacturer's instructions using the NucliSens Basic kit (Biomerieux) and primers plc-P1 and plc-P2 at 0.4 µM each. Amounts of total cellular bacterial RNA were varied, as indicated, between 0 and 2 ng. *B. anthracis* Sterne 7702 was used as a test strain and *B. thuringiensis* strain HD 621 was employed as a negative control. 1 µg of human total cellular RNA isolated from HeLa S3 cells (Stratagene) was included in all NASBA reactions to provide a complex RNA background consistent with the composition of human diagnostic samples. Following a 60 minute incubation at 41° C., NASBA reaction products were detected by using a lateral flow microarray (LFM).

Detection of NASBA Reaction Products:

Detection of NASBA products was accomplished by introducing a 2 µl aliquot of a 20 µl NASBA reaction into 8 µl of LFM running buffer (final buffer composition: 4×SSC, 0.1% SDS, 1.4% Triton X-100, 5% deionized formamide, and 0.5% w/v R-57-76-3TN coupled 0.35 µm dyed microspheres). The final volume of solution applied to LFMs was 10 µl. Following completion of sample flow, LFM membranes were allowed to air dry prior to scanning with a standard flatbed PC scanner (CanoScan 9950F, Canon, Inc.). Scans were performed at 2400 dpi resolution using 48 bit color. The resulting image files were converted to grayscale, inverted and saved as 16-bit TIFF files using Photoshop CS2 (Adobe). Image files were then analyzed using GenePix Pro 6.0 (Molecular Devices) to quantify microarray spot intensities for NASBA product detection and for dnaR89 dilution series experiments.

Results:

Prior reports have described a single nucleotide polymorphism (SNP) present in *B. anthracis* but not close phylogenetic near neighbors including *B. cereus* and *B. thuringiensis* (27, 28). This SNP has been used as the basis for a sensitive and highly discriminatory real-time PCR assay for *B. anthracis* (28). To determine the utility of LFM technology for detecting minority nucleic acids in complex samples, NASBA primers were designed to amplify the plcR allele of *B. anthracis*.

Varying amounts of total cellular RNA isolated from *B. anthracis* or 2 ng of *B. thuringiensis* HD 621 RNA as a negative control were introduced to 1 µg of total human cellular RNA isolated from HeLa S3 cells. The resulting mixtures were subjected to NASBA amplification using plc-P1 and plc-P2 primers. Human RNA was included in NASBA amplification reactions to approximate the nucleic acid complexity expected in human diagnostic specimens. 2 μl of NASBA reaction mixture was removed after a 60 minute incubation at 41° C., mixed with 8 μl of LFM running buffer and assayed for plcR amplicon by LFM. Dyed microspheres cross-linked to R-57-76-3TN were used for detection of NASBA amplicons captured on LFMs carrying R-77-96. Data from these studies are presented in FIG. 11. Following 60 minutes of NASBA amplification, as little as 0.5 pg for total cellular *B. anthracis* RNA could be detected in a background matrix of 1 μg of human total RNA. These studies closely approximate the conditions expected for complex human diagnostic samples and reveal the capacity of the LFM platform to specifically detect NASBA reaction products generated from mixed samples where the target sequence is a minority species. While the number of plcR mRNA copies in a *B. anthracis* cell has not been determined, an estimate of LFM assay sensitivity, in terms of *B. anthracis* cells, can be calculated based on total RNA yields. Total RNA yields from vegetative *B. anthracis* were in the range of approximately 167-250 fg RNA/cell. Using this value, an estimate of LFM sensitivity corresponds to the detection of approximately to 2-3 *B. anthracis* cells.

Example 9: LFMs Utilizing Semi-Conductor Nanocrystal Detection Particles Exhibit Exceptional Linear Dynamic Range To assess the impact of a fluorescent reporter on the linear dynamic range of LFM mediated analyte detection, a combined colorimetric and fluorescent detection scheme was devised. In this detection scheme, conjugated dyed microspheres as well as streptavidin conjugated fluorescent semiconductor nanocrystals (605 nm emission, Qdots, InVitrogen, Inc.) are used simultaneously as the reporter particles. For these experiments a detection oligonucleotide, R-57-76-3TBIO (5'-AGGTGAGACATAATCATG-CATTTTTTTTTU-biotinTTTTU-biotinTTTTU-biotin3') [SEQ ID O: 13], carrying three biotin-modified nucleotides was employed in hybridization sandwich assays. Following lateral flow of 250 amol of synthetic analyte dnaR89 in 10 μl of standard LFM running buffer, LFM strips were photographed under ambient light and under illumination with a hand-held UV-LED flashlight (FIG. 12).

As illustrated in FIG. 12, this detection scheme clearly allows the simultaneous visualization of hybridization events using both dyed microsphere-mediated colorimetry and semi-conductor nanocrystal-mediated fluorescent visualization even in the absence of optical filters. While excitation and emission filters may further benefit the sensitivity and signal-to-noise ratio exhibited, they are clearly not required for visualization of nanocrystal-based LFM signals.

To quantify fluorescent nanocrystal LFM signal response linearity, LFMs were challenged with 1, 5, 10, 50, 100, 500, 1000 fmol of dnaR89. Following lateral flow of these samples, LFM strips were adhered to a glass microscope slide and scanned using a standard scanning laser microarray reader (GenePix 4200 Pro, Axon Instruments). A 488 nm laser was used as the excitation source. The resulting data, shown in FIG. 13, illustrate remarkable signal linearity over the 1 fmol to 1000 fmol range of dnaR89 ($R^2$=0.991).

TABLE 1

| Function | Name | Sequence |
|---|---|---|
| Bead Conjugation/ Detection Probe | R-57-76-3TN | 5'-AGGTGAGACATA ATCATGCATTTTTTT TTTTTTTTTT-NH2-3' [SEQ ID NO: 14] |
| Detection Probe/ Negative Control | R-57-76-3N | 5'-AGGTGAGACATA ATCATGCA-NH2-3' [SEQ ID NO: 15] |
| LFM Immobilized Capture Probe | R-77-96 | 5'-TAATAAAGAGTT TGATGTGA-3' [SEQ ID NO: 16] |
| LFM Immobilized Capture Probe | R-36-55 | 5'-AAGCATTATACT TGGACAAT-3' [SEQ ID NO: 17] |

TABLE 1-continued

| Function | Name | Sequence |
|---|---|---|
| LFM Immobilized Capture Probe | R-24-43 | 5'-TGGACAATCAAT ACGAATAA-3' [SEQ ID NO: 18] |
| Synthetic target/ Positive Hyb Control | dnaR89 | 5'CAAAGCGCTTATT CGTATTGATTGTCCA AGTATAATGCTTTTG CATGATTATGTCTCA CCTTCACATCAAACT CTTTATTATCATGTA A-3' [SEQ ID NO: 19] |
| NASBA/In vitro transcription product | plcRivt | 5'-GGGAGAUUUGCA UGACAAAGCGCUUAU UCGUAUUGAUUGUCC AAGUAUAAUGCUUUU GCAUGAUUAUGUCUC ACCUUCACAUCAAAC UCUUUAUUAUCAUGU AAUACUUCUAAUUGC UUUAAUAUAUUUUCA UAUAACUCAAUACUC UUCUUAAAAUGGCCA UUUUCAGCGUAAAUG UU-3' [SEQ ID NO: 20] |
| Negative Hyb Control | FT-S18 | 5'-GCGGTCCCAAAA GGGTCAGTCGTAGCA CACCACTTTCA-3' [SEQ ID NO: 21] |
| Negative Hyb Control | F-24-43 | 5'-TTATTCGTATTG ATTGTCCA-3' SEQ ID NO: 22] |
| NASBA-P1/Allele Discrimination | plc-P1 | 5'-TTCTAATACGAC TCACTATAGGGAGAT TTGCATGACAAAGCG CTTA-3' [SEQ ID NO: 23] |
| NASBA-P2 | plc-P2 | 5'-AACATTTACGCT GAAAATGGCCA-3' [SEQ ID NO: 24] |

CITED LITERATURE

1. Huckle, D. (2006) Point-of-care diagnostics: will the hurdles be overcome this time? *Expert Rev Med Devices*, 3, 421-426.
2. Yang, S. and Rothman, R. E. (2004) PCR-based diagnostics for infectious diseases: uses, limitations, and future applications in acute-care settings. *Lancet Infect Dis*, 4, 337-348.
3. Chin, C. D., Linder, V. and Sia, S. K. (2007) Lab-on-a-chip devices for global health: past studies and future opportunities. *Lab Chip*, 7, 41-57.
4. Koch, W. H. (2004) Technology platforms for pharmacogenomic diagnostic assays. *Nat Rev Drug Discov*, 3, 749-761.
5. Mackay, I. M. (2004) Real-time PCR in the microbiology laboratory. *Clin Microbiol Infect*, 10, 190-212.
6. Cirino, N. M., Musser, K. A. and Egan, C. (2004) Multiplex diagnostic platforms for detection of biothreat agents. *Expert Rev Mol Diagn*, 4, 841-857.
7. Petrik, J. (2006) Diagnostic applications of microarrays. *Transfus Med*, 16, 233-247.
8. Heller, M. J. (2002) DNA microarray technology: devices, systems, and applications. *Annu Rev Biomed Eng*, 4, 129-153.
9. Peytavi, R., Raymond, F. R., Gagne, D., Picard, F. J., Jia, G., Zoval, J., Madou, M., Boissinot, K., Boissinot, M., Bissonnette, L. et al. (2005) Microfluidic device for rapid (<15 min) automated microarray hybridization. *Clin Chem*, 51, 1836-1844.
10. Wei, C. W., Cheng, J. Y., Huang, C. T., Yen, M. H. and Young, T. H. (2005) Using a microfluidic device for 1 microl DNA microarray hybridization in 500 s. *Nucleic Acids Res*, 33, e78.
11. Lim, D. V., Simpson, J. M., Kearns, E. A. and Kramer, M. F. (2005) Current and developing technologies for monitoring agents of bioterrorism and biowarfare. *Clin Microbiol Rev*, 18, 583-607.
12. Glynou, K., Ioannou, P. C., Christopoulos, T. K. and Syriopoulou, V. (2003) Oligonucleotide-functionalized gold nanoparticles as probes in a dry-reagent strip biosensor for DNA analysis by hybridization. *Anal Chem*, 75, 4155-4160.
13. Rule, G. S., Montagna, R. A. and Durst, R. A. (1996) Rapid method for visual identification of specific DNA sequences based on DNA-tagged liposomes. *Clin Chem*, 42, 1206-1209.
14. Dineva, M. A., Candotti, D., Fletcher-Brown, F., Allain, J. P. and Lee, H. (2005) Simultaneous visual detection of multiple viral amplicons by dipstick assay. *J Clin Microbiol*, 43, 4015-4021.
15. Kozwich, D., Johansen, K. A., Landau, K., Roehl, C. A., Woronoff, S. and Roehl, P. A. (2000) Development of a novel, rapid integrated *Cryptosporidium parvum* detection assay. *Appl Environ Microbiol*, 66, 2711-2717.
16. Zuiderwijk, M., Tanke, H. J., Sam Niedbala, R. and Corstjens, P. L. (2003) An amplification-free hybridization-based DNA assay to detect *Streptococcus pneumoniae* utilizing the up-converting phosphor technology. *Clin Biochem*, 36, 401-403.
17. Zijlmans, H. J., Bonnet, J., Burton, J., Kardos, K., Vail, T., Niedbala, R. S. and Tanke, H. J. (1999) Detection of cell and tissue surface antigens using up-converting phosphors: a new reporter technology. *Anal Biochem*, 267, 30-36.
18. Duck, P., Alvarado-Urbina, G., Burdick, B. and Collier, B. (1990) Probe amplifier system based on chimeric cycling oligonucleotides. *Biotechniques*, 9, 142-148.
19. Piepenburg, O., Williams, C. H., Stemple, D. L. and Armes, N. A. (2006) DNA detection using recombination proteins. *PLoS Biol*, 4, e204.
20. Compton, J. (1991) Nucleic acid sequence-based amplification. *Nature*, 350, 91-92.
21. Kievits, T., van Gemen, B., van Strijp, D., Schukkink, R., Dircks, M., Adriaanse, H., Malek, L., Sooknanan, R. and Lens, P. (1991) NASBA isothermal enzymatic in vitro nucleic acid amplification optimized for the diagnosis of HIV-1 infection. *J Virol Methods*, 35, 273-286.
22. Malek, L., Sooknanan, R. and Compton, J. (1994) Nucleic acid sequence-based amplification (NASBA). *Methods Mol Biol*, 28, 253-260.
23. Fong, W. K., Modrusan, Z., McNevin, J. P., Marostenmaki, J., Zin, B. and Bekkaoui, F. (2000) Rapid solid-phase immunoassay for detection of methicillin-resistant *Staphylococcus aureus* using cycling probe technology. *J Clin Microbiol*, 38, 2525-2529.
24. Baeumner, A. J., Schlesinger, N. A., Slutzki, N. S., Romano, J., Lee, E. M. and Montagna, R. A. (2002) Biosensor for dengue virus detection: sensitive, rapid, and serotype specific. *Anal Chem*, 74, 1442-1448.

25. Baeumner, A. J., Pretz, J. and Fang, S. (2004) A universal nucleic acid sequence biosensor with nanomolar detection limits. *Anal Chem*, 76, 888-894.
26. Hartley, H. A. and Baeumner, A. J. (2003) Biosensor for the specific detection of a single viable *B. anthracis* spore. *Anal Bioanal Chem*, 376, 319-327.
27. Zaytseva, N. V., Montagna, R. A., Lee, E. M. and Baeumner, A. J. (2004) Multi-analyte single-membrane biosensor for the serotype-specific detection of Dengue virus. *Anal Bioanal Chem*, 380, 46-53.
28. Edwards, K. A. and Baeumner, A. J. (2006) Optimization of DNA-tagged dye-encapsulating liposomes for lateral-flow assays based on sandwich hybridization. *Anal Bioanal Chem*, 386, 1335-1343.
29. Easterday, W. R., Van Ert, M. N., Simonson, T. S., Wagner, D. M., Kenefic, L. J., Allender, C. J. and Keim, P. (2005) Use of single nucleotide polymorphisms in the plcR gene for specific identification of *Bacillus anthracis*. *J Clin Microbiol*, 43, 1995-1997.
30. Easterday, W. R., Van Ert, M. N., Zanecki, S. and Keim, P. (2005) Specific detection of *Bacillus anthracis* using a TaqMan mismatch amplification mutation assay. *Biotechniques*, 38, 731-735.
31. Hill, K. K., Ticknor, L. O., Okinaka, R. T., Asay, M., Blair, H., Bliss, K. A., Laker, M., Pardington, P. E., Richardson, A. P., Tonks, M. et al. (2004) Fluorescent amplified fragment length polymorphism analysis of *Bacillus anthracis, Bacillus cereus*, and *Bacillus thuringiensis* isolates. *Appl Environ Microbiol*, 70, 1068-1080.
32. Pannucci, J., Cai, H., Pardington, P. E., Williams, E., Okinaka, R. T., Kuske, C. R. and Cary, R. B. (2004) Virulence signatures: microarray-based approaches to discovery and analysis. *Biosens Bioelectron*, 20, 706-718.
33. Deiman, B., van Aarle, P. and Sillekens, P. (2002) Characteristics and applications of nucleic acid sequence-based amplification (NASBA). *Mol Biotechnol*, 20, 163-179.
34. Spiro, A., Lowe, M. and Brown, D. (2000) A bead-based method for multiplexed identification and quantitation of DNA sequences using flow cytometry. *Appl Environ Microbiol*, 66, 4258-4265.
35. Albretsen, C., Haukanes, B. I., Aasland, R. and Kleppe, K. (1988) Optimal conditions for hybridization with oligonucleotides: a study with myc-oncogene DNA probes. *Anal Biochem*, 170, 193-202.
36. Schildkraut, C. (1965) Dependence of the melting temperature of DNA on salt concentration. *Biopolymers*, 3, 195-208.
37. Blake, R. D. and Delcourt, S. G. (1996) Thermodynamic effects of formamide on DNA stability. *Nucleic Acids Res*, 24, 2095-2103.
38. Baeumner, A. J., Leonard, B., McElwee, J. and Montagna, R. A. (2004) A rapid biosensor for viable *B. anthracis* spores. *Anal Bioanal Chem*, 380, 15-23.
39. Guo, Z., Guilfoyle, R. A., Thiel, A. J., Wang, R. and Smith, L. M. (1994) Direct fluorescence analysis of genetic polymorphisms by hybridization with oligonucleotide arrays on glass supports. *Nucleic Acids Res*, 22, 5456-5465.
40. Day, P. J. R., Flora, P. S., Fox, J. E. and Walker, M. R. (1991.) Immobilization of polynucleotides on magnetic particles: Factors Influencing hybridization efficiency. *Biochem. J.*, 278, 735-740.
41. O'Meara, D., Nilsson, P., Nygren, P. A., Uhlen, M. and Lundeberg, J. (1998) Capture of single-stranded DNA assisted by oligonucleotide modules. *Anal Biochem*, 255, 195-203.
42. Lane, M. J., Paner, T., Kashin, I., Faldasz, B. D., Li, B., Gallo, F. J. and Benight, A. S. (1997) The thermodynamic advantage of DNA oligonucleotide 'stacking hybridization' reactions: energetics of a DNA nick. *Nucleic Acids Res*, 25, 611-617.
43. O'Meara, D., Yun, Z., Sonnerborg, A. and Lundeberg, J. (1998) Cooperative oligonucleotides mediating direct capture of hepatitis C virus RNA from serum. *J Clin Microbiol*, 36, 2454-2459.
44. Kandimalla, E. R., Manning, A., Lathan, C., Byrn, R. A. and Agrawal, S. (1995) Design, biochemical, biophysical and biological properties of cooperative antisense oligonucleotides. *Nucleic Acids Res*, 23, 3578-3584.
45. Kieleczawa, J., Dunn, J. J. and Studier, F. W. (1992) DNA sequencing by primer walking with strings of contiguous hexamers. *Science*, 258, 1787-1791.
46. Cheek, B. J., Steel, A. B., Torres, M. P., Yu, Y. Y. and Yang, H. (2001) Chemiluminescence detection for hybridization assays on the flow-thru chip, a three-dimensional microchannel biochip. *Anal Chem*, 73, 5777-5783.
47. Roper, M. G., Easley, C. J. and Landers, J. P. (2005) Advances in polymerase chain reaction on microfluidic chips. *Anal Chem*, 77, 3887-3893.
48. Saiki, R. K., Gelfand, D. H., Stoffel, S., Scharf, S. J., Higuchi, R., Horn, G. T., Mullis, K. B. and Erlich, H. A. (1988) Primer-directed enzymatic amplification of DNA with a thermostable DNA polymerase. *Science*, 239, 487-491.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A device for detecting the presence of a target nucleic acid in a fluid sample, the device comprising:
   a porous lateral flow strip having a width of 3 mm or less; and
   a microarray of spots on said porous lateral flow strip, each spot comprising a plurality of capture oligonucleotides;
   wherein each capture oligonucleotide is complementary to a capture sequence of the target nucleic acid;
   wherein each spot was printed with a solution having a concentration of capture oligonucleotides between 200 µM and 800 µM; and
   wherein said microarray of spots provides a quantitative visual colorimetric signal indicating an amount of from 250 amol to 1 fmol of the target nucleic acid in the fluid sample comprising at least 150 mM salt in less than two minutes by capillary flow.

2. The device of claim 1 wherein said lateral flow strip comprises an area of approximately 60 mm².

3. The device of claim 1 wherein each spot has a diameter of between 50 and 300 µm.

4. The device of claim 1 wherein each spot has a diameter of between 50 and 250 µm.

5. The device of claim 1 wherein each spot has a diameter of between 50 and 200 µm.

6. The device of claim 1 wherein the porous lateral flow strip has a pore size of between 0.2 and 20 µm.

7. The device of claim 1 comprising a zone for receiving a labeled colorimetric detection oligonucleotide, which detection oligonucleotide is complementary to a detection sequence of the target nucleic acid.

8. The device of claim 7 wherein the detection oligonucleotide is a branched nucleic acid molecule or a dendrimeric nucleic acid molecule.

9. The device of claim 7 wherein the detection oligonucleotide is labeled with a detectable particle of between 0.02 and 1 µm in diameter.

10. The device of claim 9 wherein the detectable particle is selected from the group consisting of polystyrene microspheres, latex particles, nano-gold particles, colloidal gold particles, metal particles, magnetic particles, and semiconductor nanocrystals.

11. The device of claim 7 wherein a detection oligonucleotide comprises a first portion having a sequence complementary to a part of the detection sequence and a second portion having a non-target specific sequence of at least 9 nucleotides, which second portion is adjacent to a label.

12. The device of claim 11 wherein the second portion has a poly (A) or poly (T) sequence of at least 9 nucleotides.

13. The device of claim 7 wherein the capture sequence and detection sequence of the target nucleic acid are adjacent within 2 bases.

14. The device of claim 1 wherein the porous strip comprises lateral flow compatible nitrocellulose.

15. The device of claim 14 wherein said nitrocellulose has pore sizes range between 0.2 and 20 µm.

16. The device of claim 1 wherein said visual colorimetric signal is viewable by the unaided human eye.

17. The device of claim 1 comprising a sample pad and/or a conjugate release pad.

18. The device of claim 17 wherein said sample pad and/or said conjugate release pad has been impregnated with a substance selected from the group consisting of 4-1(1,1,3,3-Tetramethylbutyl)phenyl-polyethylene glucol, SDS, BSA, a hydrophilic polysaccharide, polyvinyl pyrolidone, and combinations thereof.

* * * * *